US010607736B2

United States Patent
Eggebraaten et al.

(10) Patent No.: US 10,607,736 B2
(45) Date of Patent: Mar. 31, 2020

(54) EXTENDING MEDICAL CONDITION BASE CARTRIDGES BASED ON SME KNOWLEDGE EXTENSIONS

(71) Applicant: International Business Machines Corporation, Armonk, NY (US)

(72) Inventors: Thomas J. Eggebraaten, Rochester, MN (US); Mark G. Megerian, Rochester, MN (US); Richard J. Stevens, Monkton, VT (US)

(73) Assignee: International Business Machines Corporation, Armonk, NY (US)

( * ) Notice: Subject to any disclaimer, the term of this patent is extended or adjusted under 35 U.S.C. 154(b) by 423 days.

(21) Appl. No.: 15/350,532

(22) Filed: Nov. 14, 2016

(65) Prior Publication Data

US 2018/0137249 A1    May 17, 2018

(51) Int. Cl.
*G16H 50/20* (2018.01)
*G16H 10/60* (2018.01)
*G16H 50/70* (2018.01)
*G16H 70/20* (2018.01)

(52) U.S. Cl.
CPC ............ *G16H 50/20* (2018.01); *G16H 10/60* (2018.01); *G16H 50/70* (2018.01); *G16H 70/20* (2018.01)

(58) Field of Classification Search
CPC ........ G16H 50/20; G16H 10/60; G16H 50/70; G16H 70/20
See application file for complete search history.

(56) References Cited

U.S. PATENT DOCUMENTS

| 5,839,438 A | 11/1998 | Graettinger et al. |
| 6,063,028 A | 5/2000 | Luciano |
| 6,248,063 B1 | 6/2001 | Barnhill et al. |
| 7,233,892 B2 | 6/2007 | Brill et al. |
| 8,275,803 B2 | 9/2012 | Brown et al. |
| 8,473,489 B1 | 6/2013 | Lasko et al. |
| 8,868,472 B1 | 10/2014 | Lin et al. |

(Continued)

OTHER PUBLICATIONS

Miotto, Deep Patient: An Unsupervised Representation to Predict the Future of Patients from the Electronic Health Records, May 17, 2016, Scientific Reports, pp. 1-10. (Year: 2016).*

(Continued)

*Primary Examiner* — Christopher L Gilligan
(74) *Attorney, Agent, or Firm* — Stephen J. Walder, Jr.; Ryan G. Lewis

(57) ABSTRACT

Mechanisms are provided for extending a medical condition base cartridge (MCBC) based on user modifications of the MCBC. The mechanisms generate a MCBC for a medical condition at least by performing cognitive processing of natural language content in a corpus to extract patient attributes and treatment information associated with the medical condition. Information stored in the MCBC is presented to a user via at least one interface and user input is received, where the user input indicates at least one of a modification of, addition to, or deletion of, a portion of the information presented to generate an extension to the MCBC. The extension to the MCBC is stored as an expert medical condition cartridge (EMCC) in association with the MCBC in a repository. The EMCC is input to a medical cognitive system to perform a medical cognitive operation on patient information based on the EMCC.

20 Claims, 12 Drawing Sheets

(56) References Cited

U.S. PATENT DOCUMENTS

| | | | |
|---|---|---|---|
| 9,298,880 | B2 | 3/2016 | Vilsmeier et al. |
| 9,336,497 | B2 | 5/2016 | Baughman et al. |
| 9,779,611 | B1 | 10/2017 | Krayer et al. |
| 10,340,034 | B2 | 7/2019 | Hyde et al. |
| 2003/0105638 | A1 | 6/2003 | Taira |
| 2003/0163353 | A1 | 8/2003 | Luce et al. |
| 2007/0094188 | A1 | 4/2007 | Pandya et al. |
| 2008/0171916 | A1 | 7/2008 | Feder et al. |
| 2008/0201280 | A1 | 8/2008 | Martin et al. |
| 2009/0006131 | A1 | 1/2009 | Unger et al. |
| 2009/0156906 | A1 | 6/2009 | Liebman et al. |
| 2009/0287678 | A1 | 11/2009 | Brown et al. |
| 2010/0169219 | A1 | 7/2010 | Sellers et al. |
| 2010/0234236 | A1 | 9/2010 | Cohen et al. |
| 2011/0046979 | A1* | 2/2011 | Tulipano ............... G06F 19/325 705/2 |
| 2011/0066587 | A1 | 3/2011 | Ferrucci et al. |
| 2011/0125734 | A1 | 5/2011 | Duboue et al. |
| 2012/0016690 | A1 | 1/2012 | Ramarajan et al. |
| 2013/0007055 | A1 | 1/2013 | Brown et al. |
| 2013/0018652 | A1 | 1/2013 | Ferrucci et al. |
| 2013/0066886 | A1 | 3/2013 | Bagchi et al. |
| 2013/0132312 | A1 | 5/2013 | Lee et al. |
| 2013/0226616 | A1 | 8/2013 | Nigam et al. |
| 2014/0046889 | A1 | 2/2014 | Biem et al. |
| 2014/0058738 | A1 | 2/2014 | Yeskel |
| 2014/0073882 | A1 | 3/2014 | Choi et al. |
| 2014/0081898 | A1* | 3/2014 | Saigal .................... G06N 5/048 706/52 |
| 2014/0113263 | A1 | 4/2014 | Jarrell et al. |
| 2014/0337051 | A1* | 11/2014 | Karpf ..................... G06F 19/00 705/3 |
| 2014/0365232 | A1 | 12/2014 | Sadeghi |
| 2015/0019241 | A1 | 1/2015 | Bennett et al. |
| 2015/0066537 | A1 | 3/2015 | Sheffer et al. |
| 2015/0066539 | A1 | 3/2015 | Sheffer et al. |
| 2015/0118661 | A1 | 4/2015 | Haruta et al. |
| 2015/0302167 | A1 | 10/2015 | Vali et al. |
| 2015/0356270 | A1 | 12/2015 | Devarakonda et al. |
| 2015/0363559 | A1 | 12/2015 | Jackson et al. |
| 2015/0370982 | A1 | 12/2015 | Zien et al. |
| 2016/0063212 | A1 | 3/2016 | Monier et al. |
| 2016/0070867 | A1 | 3/2016 | Zhang et al. |
| 2016/0078039 | A1 | 3/2016 | Baughman et al. |
| 2016/0110501 | A1 | 4/2016 | Allen et al. |
| 2016/0358290 | A1 | 12/2016 | Chiu et al. |
| 2017/0262587 | A1 | 9/2017 | Agarwal et al. |

OTHER PUBLICATIONS

List of IBM Patents or Patent Applications Treated as Related, May 2, 2017, 2 pages.

"LarKC: the Large Knowledge Collider", http://www.larkc.org/overview/index.html, Accessed from the Internet on May 12, 2016, 4 pages.

"The Era of Cognitive Systems: An inside look at IBM Watson and how it works", IBM Corporation, IBM Software Group, Whitepaper, IBM Watson Solutions, Sep. 2012, 19 pages.

Baum, Stephanie, "Could an EMR plugin using big data help physicians make diagnosis more efficient?", MedCityNews, Jul. 9, 2013, 9 pages.

Choi, Wonjun et al., "HerDing: herb recommendation system to treat diseases using genes and chemicals", Oxford University Press, Jan. 2016, 7 pages.

Deleger, Louise et al., "Building Gold Standard Corpora for Medical Natural Language Processing Tasks", AMIA Annual Symposium Proceedings 2012, Nov. 3, 2012, pp. 144-153.

Denmer-Fushman, Dina et al., "What can Natural Language Processing do for Clinical Decision Support?", J Biomed. Inform., 42(5), Oct. 2009, 29 pages.

Gotz, David et al., "ICDA: A Platform for Intelligent Care Delivery Analytics", Proceedings of AMIA Annual Symposium, Nov. 12, 2012, 10 pages.

High, Rob, "The Era of Cognitive Systems: An Inside Look at IBM Watson and How it Works", IBM Corporation, Redbooks, Dec. 12, 2012, 16 pages.

Hussein, Asmaa et al., "Accurate and Reliable Recommender System for Chronic Disease Diagnosis", Global Health 2012: The First International Conference on Global Health Challenges, Oct. 2012, pp. 113-118.

Lim, Thean Pheng et al., "Recommender System for Personalised Wellness Therapy", International Journal of Advanced Computer Science and Applications (IJACSA), vol. 4, No. 9, Oct. 2013, pp. 54-60.

Mahdavi, Meisamshabanpoor and Mehregan, "Implementation of a Recommender System on Medical Recognition and Treatment", International Journal of e-Education, e-Business, e-Management and e-Learning, vol. 2, No. 4, Aug. 2012, pp. 315-318.

Mccord, M.C. et al., "Deep parsing in Watson", IBM J. Res. & Dev. vol. 56 No. 3/4 Paper 3, May/Jul. 2012, pp. 3:1-3:15.

Sjobergh, Jonas et al., "Visualizing Clinical Trial Data Using Pluggable Components", 16th International Conference on Information Visualization, Jul. 11-13, 2012, 6 pages.

Sodsee, Sunantha et al., "Evidence-based Medical Recommender Systems: A Review", International Journal of Information Processing and Management, vol. 4, No. 6, Sep. 2013, pp. 114-120.

Wall, Dennis P. et al., "Genotator: A disease-agnostic tool for genetic annotation of disease", BMC Medical Genomics, Oct. 2010, 10 pages.

Wiesner, Martin et al., "Health Recommender Systems: Concepts, Requirements, Technical Basics and Challenges", International Journal of Environmental Research and Public Health, Mar. 3, 2014, 28 pages.

Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

"Quantitative Pros and Cons", Website printout, archived on Aug. 13, 2016, 4 pages.

* cited by examiner

| CARTRIDGE > NCCN-BASED KIDNEY CANCER > INCLUSION / EXCLUSION | | | | | | |
|---|---|---|---|---|---|---|
| ORDER | TYPE | FACTOR | TREATMENTS | CRITERIA | ACTIONS | ACTIONS |
| 1 | EXCLUSION | 0.5 | CONTAINS: HIGH DOES INTERLEUKIN-2, CODES: 71501 | PERFORMANCESTATUS IN [2.0, 5.0] | ✎ ● ▭ | ⇦ ⇨ |
| 2 | EXCLUSION | 0.5 | CONTAINS: BEVACIZUMAB | CARDIOVASCULAR FUNCTION RISK= YES | ✎ ● ▭ | ⇦ ⇨ |
| 3 | EXCLUSION | 0.5 | CONTAINS: BEVACIZUMAB | HYPERTENSION = YES | ✎ ● ▭ | ⇦ ⇨ |
| 4 | EXCLUSION | 0.5 | CONTAINS: SUNITINIB | CARDIOVASCULAR FUNCTION RISK= YES | ✎ ● ▭ | ⇦ ⇨ |
| 5 | EXCLUSION | 0.5 | CONTAINS: TEMSIROLIMUS | UNCONTROLLED DIABETES = YES | ✎ ● ▭ | ⇦ ⇨ |
| 6 | EXCLUSION | 0.9 | CONTAINS: HIGH DOSE INTERLEUKIN-2 | CARDIOVASCULAR FUNCTION RISK= YES | ✎ ● ▭ | ⇦ ⇨ |
| 7 | EXCLUSION | 0.5 | CONTAINS: PAZOPANIB  930 | CARDIOVASCULAR FUNCTION RISK= YES | ✎ ● ▭ | ⇦ ⇨ |
| 8 | EXCLUSION | 0.3 | CONTAINS: PAZOPANIB | HYPERTENSION = YES | ✎ ● ▭ | ⇦ ⇨ |

*FIG. 9B*

CARTRIDGE > NCCN-BASED KIDNEY CANCER > DERIVED ATTRIBUTES

| ORDER | DERIVED ATTRIBUTES | VALUE | CRITERIA | ACTIONS | ACTIONS |
|---|---|---|---|---|---|
| 1 | RESELECTABLEANDSURGICALCANDIDATE | YES | SURGICALCANDIDATE=YES AND RESELECTABLE=YES | ◇ ○ ▣ | ⇦ ⇨ |
| 2 | RESELECTABLEANDSURGICALCANDIDATE | NO | SURGICALCANDIDATE=YES AND RESELECTABLE=NO | ◇ ○ ▣ | ⇦ ⇨ |
| 3 | RESELECTABLEANDSURGICALCANDIDATE | NO | SURGICALCANDIDATE=NO AND RESELECTABLE=YES | ◇ ○ ▣ | ⇦ ⇨ |
| 4 | RESELECTABLEANDSURGICALCANDIDATE | NO | SURGICALCANDIDATE=NO AND RESELECTABLE=NO | ◇ ○ ▣ | ⇦ ⇨ |
| 5 | RESELECTABLEANDSURGICALCANDIDATE | YES | RESELECTABLEANDSURGICALCANDIDATE = NULL | ◇ ○ ▣ | ⇦ ⇨ |
| 6 | RELAPSE | NO | PRIOR THERAPIES = NONE | ◇ ○ ▣ | ⇦ ⇨ |
| 7 | RELAPSE | YES | PRIOR THERAPIES = NONE | ◇ ○ ▣ | ⇦ ⇨ |
| 8 | IST1A | YES | TUMOR PATHOLOGICAL CLASSIFICATION = PT1A | ◇ ○ ▣ | ⇦ ⇨ |
| 9 | HADTKI | YES | PRIORTARGETEDREGIMEN= [71200, 71201, 71202, 71203, 71204, 71205, 71206, 71207, 71208, 71209] | ◇ ○ ▣ | ⇦ ⇨ |

EXTENDING MEDICAL CONDITION BASE CARTRIDGES BASED ON SME KNOWLEDGE EXTENSIONS

BACKGROUND

The present application relates generally to an improved data processing apparatus and method and more specifically to mechanisms for extending medical condition base cartridges for a medical system based on subject matter expert (SME) knowledge extensions.

Decision-support systems exist in many different industries where human experts require assistance in retrieving and analyzing information. An example that will be used throughout this application is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to cause the at least one processor to implement the method. The method comprises generating, by the data processing system, a medical condition base cartridge (MCBC) comprising basic insight data structures for a medical condition at least by performing cognitive processing of natural language content in a corpus to extract patient attributes and treatment information associated with the medical condition. The method further comprises presenting, by the data processing system, to a user, information stored in the basic insight data structures of the MCBC, via at least one interface. The method also comprises receiving, by the data processing system, user input to the at least one interface, the user input indicating at least one of a modification of, addition to, or deletion of, a portion of the information presented to generate an extension to the MCBC. Furthermore, the method comprises storing, by the data processing system, the extension to the MCBC as an expert medical condition cartridge (EMCC) in association with the MCBC in a repository. In addition, the method comprises inputting, by the data processing system, the EMCC to a medical cognitive system to perform a medical cognitive operation on patient information based on the EMCC.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIGS. 9A-9C are example diagrams of graphical user interfaces associated with SME extension tools in accordance with one illustrative embodiment.

DETAILED DESCRIPTION

Figure 1:
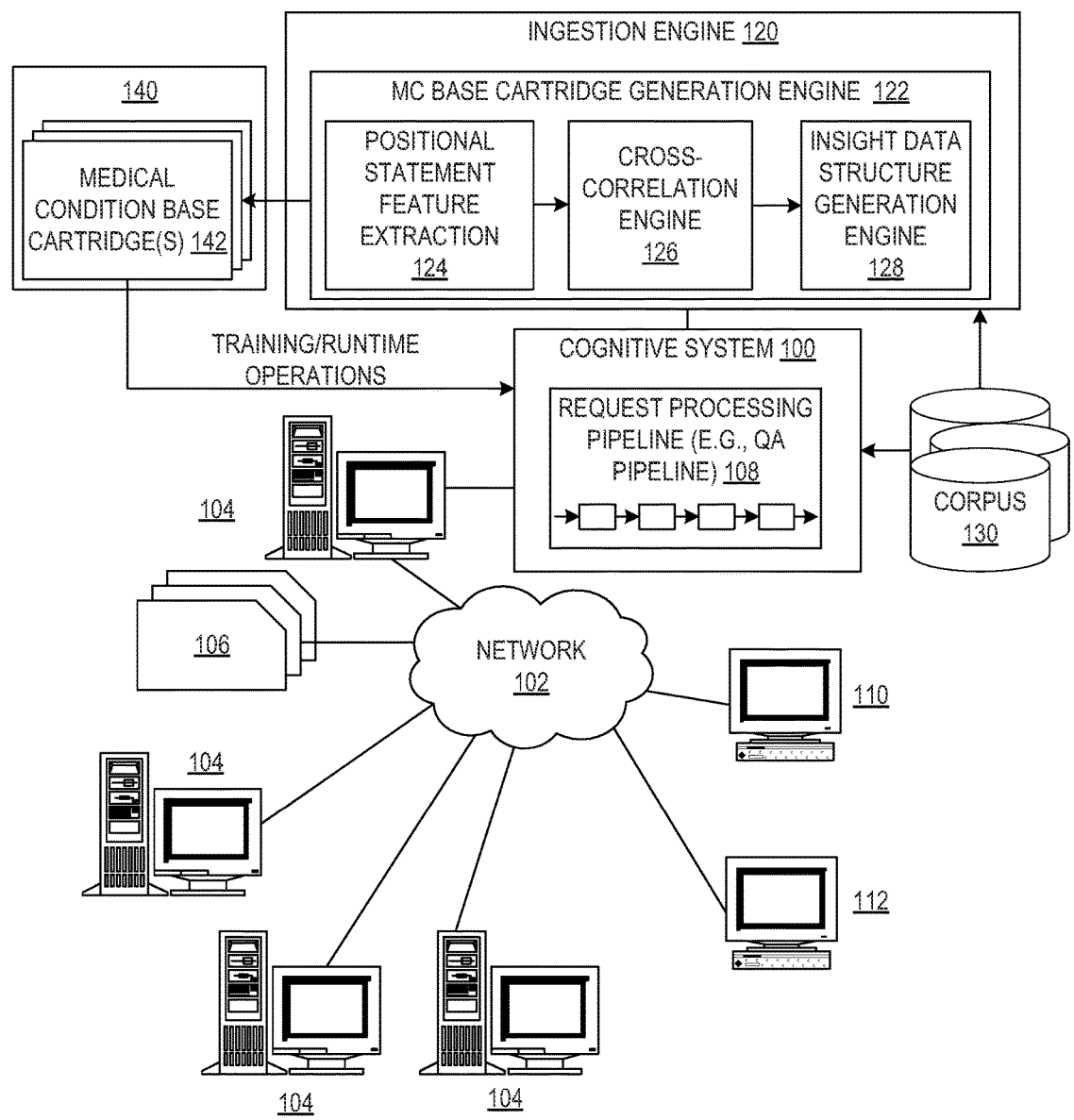
FIG. 1 depicts a schematic diagram of one illustrative embodiment of a cognitive system in a computer network.

The strengths of current medical diagnosis, patient health management, and patient treatment recommendation systems are that they can improve medical practitioners' diagnostic hypotheses, can help medical practitioners avoid missing important diagnoses, and can assist medical practitioners with determining appropriate treatments for specific diseases. However, current systems still suffer from significant drawbacks which should be addressed in order to make such systems more accurate and usable for a variety of healthcare applications as well as more representative of the way in which human healthcare practitioners diagnose and treat patients. In particular, one drawback of current systems is that they are designed, trained, and configured for use with a small predefined set of medical conditions and/or for a particular subset of medical institutions/practitioners.

For example, medical treatment recommendation systems must be trained and configured to provide treatment recommendations based on machine learning for each possible medical condition and corresponding treatment with which they are intended to operate. When building a treatment recommendation system, initially a set of training cases may be utilized that represents the treatment practices of a particular institution and/or set of doctors for a particular medical condition. This training set forms the basis of a ground truth that the treatment recommendation system strives to replicate through the machine learning process. Through feature engineering, machine learning, iterative improvements, and ongoing knowledge transfer with human subject matter experts, the system is trained to be able to achieve high levels of accuracy in matching the ground truth. If the treatment recommendation system has the proper inputs that are extracted from a subsequent case, e.g., patient electronic medical records (EMRs), either via natural language processing against unstructured text, or directly from structured patient attributes, the treatment recommendation system applies the same considerations as the human subject matter expert as specified through the training, and the treatment recommendation system has the correct domain of possible answers, the treatment recommendation system can approximate the thinking of the subject matter experts (SMEs) since the machine learning process will apply appropriate weights to the various scoring features that have been developed through the training of the system.

This training of the treatment recommendation system works well for individual combinations of medical conditions and their associated treatments. However, if a treatment recommendation system is to support treatment recommendation operations for a large number of different medical conditions, then the treatment recommendation system would need to be trained for each separate medical condition, e.g., disease or other medical malady. In other words, treatment recommendation systems are trained using a very disease-specific and patient attributes-specific based training that results in a complex model with a requirement for a large volume of training cases. For example, there may be features of lung-platinum-therapy, liver-dysfunction-comorbidity, or alopecia-avoidance, or any other very specific medical condition, treatment, and patient attributes and all of these features and their possible combinations must be considered during training of the treatment recommendation system so that future treatment recommendations may be made accurately when encountering similar features or combinations of features in subsequent cases.

The requirements for such large scale and complex training of treatment recommendation systems leads to a large outlay of resources to build and train these systems, or if such large amounts of resources are not invested, then this leads to systems that have overly limited use. Moreover, the resulting trained system is still inflexible to new treatments, medical conditions, and patient attributes being introduced, new correlations of such features being discovered, or the like, since this would require retraining of the treatment recommendation system.

Moreover, much of the training of such systems is still manual in nature. That is, it is the responsibility of human subject matter experts (SMEs) to manually build the knowledge base, training sets, and the like, for individual medical conditions such that the treatment recommendation system is able to be configured and trained to provide treatment recommendations for patients. This process requires the human SME to input information about the medical condition, information about how to diagnose the medical condition, information about the possible treatments, information defining the criteria for application of the possible treatments to patients diagnosed with the medical condition, information about the application of the treatment to patients, etc. This requires a large amount of effort on the part of human SMEs to manually provide such information.

To address these drawbacks, the illustrative embodiments provide mechanisms for automatic cognitive building of a medical condition knowledge structure, referred to herein as a "medical condition base cartridge," based on cognitive ingestion of structured and/or unstructured content from an electronic corpus or corpora, e.g., one or more databases or repositories of electronic documents or data structures that comprise information content. In some illustrative embodiments, the medical condition knowledge structure, or medical condition base cartridge, is generated by parsing and analyzing electronic natural language documents or data structures (referred to herein as "documents" or "natural language documents") present in the electronic corpus or corpora, which may include positional statements from medical condition treatment guideline documents. The information extracted from such natural language documents is correlated with patient cohort information, pharmaceutical information, clinical attributes, and the like, which may be specified in the natural language documents.

The result is a knowledge structure, i.e. medical condition base cartridge, that comprises a representation of the knowledge associated with a medical condition, the possible treatments for that medical condition, the primary attributes of the patients which are relevant to the medical condition, primary attributes of the medical condition, primary attributes of the treatments for the medical condition, the criteria for each treatment, any supporting evidence or links to supporting evidence in the electronic corpus/corpora that is used to build the medical condition base cartridge, rationale and various other information that assists a cognitive medical system in performing its operations, and the like. This may be done for a plurality of different medical conditions. The resulting medical condition base cartridges may then be plugged into a framework associated with the cognitive medical system that will make use of these medical condition base cartridges. The medical condition base cartridges may then be used to train the cognitive medical system and/or may be used to perform runtime operations, such as providing treatment recommendations for patients or other decision support operations.

Thus, in accordance with one aspect of the illustrative embodiments, mechanisms are provided for generating pluggable medical condition base cartridges that provide the basic knowledge for evaluating input factors to generate various decision support outputs regarding a medical condition. These medical condition base cartridges provide mechanisms for implementing in logic the base knowledge for a medical condition, e.g., knowledge from standards documents and treatment guidelines, many times subject matter experts have knowledge that may not be reflected in this base knowledge.

In a further aspect of the illustrative embodiments, mechanisms are provided for extending the medical condition base cartridge based on subject matter expert (SME) knowledge extensions. A SME is a human being that has specific knowledge with regard to a medical condition or class of medical conditions and can provide additional insights and knowledge regarding the medical condition, patient attributes of specific importance to the medical condition and/or its treatments, particular treatments for the medical condition, or the like. For example, a SME may be a medically trained individual, such as a doctor, nurse, or the like. As such, the SME may not be technically trained with regard to computing systems, such that the SME has little or no knowledge of how to implement computer logic for performing cognitive operations. However, the illustrative embodiments provide mechanisms through which a SME may extend the automatically generated logic for a medical condition evaluation by a cognitive medical system, via automatically generated foundational medical condition base cartridges, to implement their own personal expertise and knowledge regarding the medical aspect of the cognitive medical evaluation, without having to have technical knowledge of how to implement such in a cognitive computing system.

In accordance with one or more of the illustrative embodiments, where the medical condition base cartridge provides a foundation of knowledge for a particular medical condition, extensions of this foundation are made by a SME using tools provided to the SME for modifying or extending the medical condition base cartridge and thereby generate an expert medical condition cartridge. Because the SME knowledge is built on top of the foundational medical condition base cartridge, it may be easily replaced or modified by other SMEs while maintaining the medical condition base knowledge set forth in the medical condition base cartridge.

Essentially, the generation of the medical condition base cartridge may be performed without having to have specific institutional expertise in a particular medical condition since the knowledge represented by the medical condition base cartridge is obtained automatically from a corpus of corpora of electronic documentation, such as treatment guidelines, positional statements in trusted documentation, and the like. Given this foundation, a SME needs to only make modifications to the foundation to layer on top of the foundation their own personal expertise and knowledge regarding the particular medical condition and/or treatments for the medical condition.

For example, where a medical condition base cartridge may indicate that a particular patient attribute is more strongly indicative of a particular treatment being appropriate for the medical condition, the SME may, based on their own particular knowledge, know that this patient attribute is not as significant as the documentation used to generate the medical condition base cartridge would seem to suggest, and may modify the weighting or strengths associated with that patient attribute and the corresponding treatment. Moreover, a SME may determine that some patient attributes were not included as factors when determining whether a particular treatment is appropriate or not, and may add those patient attributes along with a relative weighting or strength, contraindications, and the like. Still further, a SME may know that certain medications that are part of a treatment for a particular medical condition may negatively interact with other medications and may add such information to the knowledge of the medical condition base cartridge. Many different tools may be provided to the SME to adjust, modify, remove, or add elements to the medical condition base cartridge via easily usable interfaces, with the computing system logic performing the work of translating the SME input into new, modified, or removed elements of the medical condition cartridge. The SME modifications may be stored as an expert medical condition cartridge in a medical condition cartridge repository. The expert medical condition cartridge may be stored as a separate and distinct structure from the medical condition base cartridge but including the medical condition base cartridge as a foundation, as a layered addition to the medical condition base cartridge that may be enabled/disabled, or as a separate extension data structure and logic that is linked to the medical condition base cartridge such that it may be retrievable when necessary.

In this way, a large majority of the work required to generate logic for evaluating a medical condition is performed automatically by the mechanisms of the illustrative embodiment such that a knowledge structure for a medical condition providing a foundational knowledge from documentation may be generated. Further mechanisms allow for a relatively smaller expenditure of effort on the part of a SME to augment this foundational knowledge by providing the SME's own expert knowledge as an extension of this automatically generated foundational knowledge about the medical condition and its treatment options. Moreover, the foundational knowledge is reusable by various SMEs such that each SME may tailor the knowledge of a medical condition to their own experiences.

The result is a methodology, computer program product, and system in which an efficient, rapid, and repeatable process for building knowledge about medical conditions and their treatments is provided. One can quickly develop a pluggable, and reusable, medical condition base cartridge from standard documents, positional statements, and guidelines for a medical condition without requiring any commitments from a particular institution or SME. Thereafter, SMEs may tailor the foundational knowledge of the pluggable, and reusable, medical condition base cartridge to their own personal experiences, knowledge, and expertise via tools that allow for the SMEs to extend the medical condition base cartridge.

As a result of the implementation of tools for extending medical condition base cartridges with SME supplied expert information based extensions, when later being used to evaluate a patient, a user may choose to enable/disable the use of SME expert medical condition cartridges. In addition, the user may select to enable/disable specific SME expert medical condition cartridges. For example, a repository of expert medical condition cartridges may be provided and particular ones of these expert medical condition cartridges, sets of expert medical condition cartridges, expert medical condition cartridges associated with a particular SME, expert medical condition cartridges associated with particular classes or types of medical conditions, and the like, may be selected for use with a cognitive medical system. In this way, a user may designate whether to use medical condition base cartridges, expert medical condition cartridges, or a combination of the two, when performing evaluation of patient's information to perform a cognitive operation on the patient's information, e.g., generating a treatment recommendation.

As an example, a particular SME, e.g., Doctor Smith, may have a reputation as a renowned expert in the field of a particular medical condition and Doctor Smith's extensions to medical condition base cartridges may be preferred over others. As a result, a user may select the expert medical condition cartridges (EMCCs) that are associated with Doctor Smith. Similarly, particular institutions may be known for their expertise in different fields of medical research and treatment and thus, may be preferred over others with regard to certain medical conditions. As a result, their associated EMCCs may be preferred when evaluating a patient with regard to a corresponding medical condition. The user is able to select any desirable set of EMCCs or medical condition base cartridges that they wish to employ in the cognitive medical system without departing from the spirit and scope of the present invention.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for automatically and cognitively building a medical condition base cartridge for a medical condition that sets forth the knowledge about a medical condition and its treatments, such that this information may be used by a cognitive medical system, such as a cognitive medical treatment recommendation engine, decision support system, or the like. In some illustrative embodiments, the mechanisms of the illustrative embodiments generate the medical condition base cartridge based on a parse of natural language documentation, such as positional statements from medical treatment guideline documents. The medical condition base cartridge, also referred to herein as simply the "base cartridge," comprises a structured representation of the knowledge, possible treatments, primary clinical attributes, treatment criteria, supporting evidence, rationale and various other information that helps a cognitive medical system perform cognitive medical operations, such as medical treatment recommendations and providing decision support, such as by providing supporting evidence and other insight statements as an output to a user or decision maker (e.g., a physician or other medical personnel).

Any suitable cognitive medical operation may be performed by the cognitive medical system based on the base cartridges used by the cognitive medical system. One example of such a cognitive medical operation may include, but is not limited to, determining a range of treatment options that are preferred, acceptable, or not recommended based on the values of clinical attributes. In addition, a list of relevant supporting evidence publications for each treatment option may be determined based on the clinical attribute values and the associated treatment. Medical logic may also be used to perform complex attribute derivations based on the values of other attributes. Medical logic may be programmed so that a certain set of symptom attributes, when present, cause another attribute which represents a particular grade of a medical condition to be set. For example, the cognitive medical operation may be generating medical observations, generating diagnoses from diagnosis tests, evaluating a medical condition of the patient based on medical lab tests, monitoring the medical condition of a patient, generating a medical treatment recommendation (it should be appreciated that a medical treatment recommendation may not be limited to recommending a treatment to be administered and may in fact represent a recommendation to stop or modify a treatment, or the like). Many different types of cognitive medical operations may be performed in accordance with one or more of the illustrative embodiments.

With the mechanisms of the illustrative embodiments, natural language parsing, feature extraction, and analysis of natural language documents is performed to identify features, including medical condition information, treatment information, pharmaceutical information, patient attributes, and the like, associated with a particular medical condition, e.g., disease. For example, natural language processing may be performed on a medical treatment guidelines document to identify each of the positional statements, which correlate medical condition attributes, patient attributes, treatment attributes, and the like, in the medical treatment guideline document associated with their corresponding particular medical conditions. For example, a medical treatment guidelines document may be published by a trusted source, e.g., accredited medical organization, governmental agency, pharmaceutical company, medical journal or other trusted publication, hospital or other medical facility, or the like, which indicates various treatments with regard to one or more particular medical conditions, and the various attributes of the patients, the attributes of the medical treatment, and the medical condition associated with that medical treatment, e.g., the medical treatment guideline document may set forth a plurality of treatments for Type 2 Diabetes and indicate the particular types of patients (e.g., the collection of patient attributes) for which the different treatments are applicable, the conditions under which they are applicable, and the manner by which the treatment is to be administered to the patient, as well as any warnings or other guidance to be given to the patient as part of the treatment.

Alternatively, the medical treatment guidelines document may set forth information about a particular treatment and the various medical conditions for which the treatment is applicable, the various types of patients for which the treatment is applicable, and the conditions under which to provide the treatment as well as the manner by which to provide the treatment, e.g., a particular treatment may be applicable to multiple different medical conditions and/or multiple different types of patients under various conditions with corresponding potential differences in the manner by which the medical treatment is to be administered. Any configuration of medical treatment guideline document is intended to be able to be used with the mechanisms of the illustrative embodiments. Since the mechanisms of the illustrative embodiments implement natural language processing techniques to extract features from the natural language content, the mechanisms of the illustrative embodiments are amenable to any configuration of natural language content and are not limited to structured content.

In general, the medical treatment guideline documents are comprised of positional statements which are natural language statements that set forth the medical condition, the treatment, and the conditions under which the treatment is applicable/not applicable for treating the medical condition. These conditions may be presented in terms of patient attributes, medical condition attributes, and/or other attributes associated with the patient, medical condition, or even the treatment itself. For example, a positional statement in a medical treatment guideline document may be of the type "You should prescribe drug Z, 1 pill per day, for female patients diagnosed with type 2 diabetes, who are 50 years old or older, and have a persistent rash." Patient attributes, treatment attributes, medical condition attributes, and the like, are extracted from such positional statements and converted to an insight data structure which defines the logic present in the medical condition base cartridge for use by a cognitive medical system.

For example, treatment features of "drug Z" and "1 pill per day" are extracted from the example positional statement, medical condition attributes of "Type 2 diabetes" and "persistent rash" are extracted from the example positional statement, and patient attributes of "female" and age of "50 years old or older" are extracted from the example positional statement.

In some illustrative embodiments, the positional statements in a treatment guideline document may also be associated with a grading value which has been assigned to the positional statement by an oversight organization, as will be described hereafter. The grading may be provided in the natural language content of the medical treatment guideline document itself or may be part of metadata that associates the grading value with the particular positional statement within the medical treatment guideline document. In some cases, a general grading may be provided for the entire document such that it applies to all of the positional statements set forth in the medical treatment guidelines document. Regardless of the particular implementation, the grading value for a positional statement is identified, extracted, and included in the insight data structure that is generated from the positional statement.

The various types of attributes extracted from such positional statements are collectively referred to herein as "clinical attributes" meaning that they are attributes directed to patients, their medical conditions, and treatments for those medical conditions from a clinical viewpoint. Clinical attributes are only one type of feature that may be extracted through natural language processing of such positional statements and guideline documents, while other features may be utilized in addition to, or in replacement of, clinical attributes depending on the particular implementation and the particular medical conditions being represented by the base cartridge. That is, the features may vary by medical condition and thus, by base cartridge. For example, a diabetes base cartridge has features describing blood sugar, A1C, and the like, while a cancer base cartridge may have features related to cancer stage, tumor location, lymph node involvement, and the like. Still further, other features may include the positional statement grading values as mentioned above, types of testing or experiments that back up a positional statement, the governing body that issued the positional statement, the type of clinical trial used in establishing the results set forth in the positional statement, the degree of certainty with a clinical attribute's relationship with the medical condition and/or treatment or a specified value of the clinical attribute, a priority associated with the positional statement, an importance level associated with the positional statement, or the like. These may also be referred to as guidance information to assist with an understanding of the positional statement.

The various clinical attributes and other features may be extracted through natural language processing of the positional statements which may perform semantic and syntactic analysis of the natural language to look for key terms/phrases indicative of the various clinical attributes and may classify them into different types of clinical attributes, e.g., "medical condition", "symptom", various patient attributes including "gender", "age", "ethnicity", etc., "treatment", "dosage", etc. Thus, each clinical attribute extracted from the positional statement may be associated with a corresponding clinical attribute type which can be used by a cognitive medical system to perform cognitive medical operations.

The extraction and classification of clinical attributes may be used as a basis for generating insight data structures that are stored as part of the medical condition base cartridge for defining a treatment for a medical condition. The medical condition base cartridge may be specific for a particular medical condition and thus, may have multiple insight data structures, each corresponding to a treatment for the same medical condition, e.g., a medical condition base cartridge for "Type 2 Diabetes" may have multiple entries of insight data structures, where each entry corresponds to a particular treatment for Type 2 Diabetes. In some cases, the medical condition base cartridge may be more general in nature and may cover a variety of medical conditions associated with a more general classification of medical conditions, e.g., a "diabetes" medical condition base cartridge, a "blood cancer" medical condition base cartridge, a "podiatry" medical condition base cartridge, etc. Essentially, the medical condition base cartridge provides a structured representation of knowledge about one or more related medical conditions and their corresponding treatments, as extracted from natural language content of a corpus or corpora.

As noted above, the medical condition base cartridge comprises structured representations of knowledge about a medical condition in the form of insight data structures generated from the natural language processing of the positional statements in the ingested medical treatment guidelines documents. As an example, using the Type 2 Diabetes positional statement example mentioned above, the extracted clinical attributes/features may be combined to form an insight data structure of the type {medical condition=Type 2 diabetes, symptom=persistent rash, gender=female, age>=50, treatment=drug Z, dosage=1 pill per day}, for example.

The clinical attributes/features extracted from natural language positional statements may be cross-correlated with other clinical attributes/features in the medical treatment guideline document itself, other medical treatment guideline documents of the corpus or corpora, other medical knowledge resources such as structured databases of patient/medical condition/treatment information, and with pharmaceutical information, such as drug label information in drug databases or other knowledge databases. The resulting clinical attributes/features obtained from these other sources, clinical attributes/features obtained from positional statements in the medical treatment guideline document being ingested, and pharmaceutical information, may be aggregated together to generate one or more insight data structures, e.g., combinations of clinical attributes and features that may be interpreted as logical rules, supporting evidential information, patient guidance information (e.g., do not be exposed to direct sunlight, do not handle heavy machinery, etc.), and the like, to thereby generate entries in the medical condition base cartridge for each potential treatment for the medical condition corresponding to the medical condition base cartridge.

The cross-correlation of attributes/features extracted from the ingestion of a portion of natural language content, e.g., a positional statement, may take many different forms depending on the particular implementation. For example, from the positional statement ingestion, the mechanisms of the illustrative embodiments obtain information regarding the correlation between patient attributes, medical condition attributes, and treatment attributes. This same pattern of attributes/features, or subsets of such attributes/features, may be searched for in other documents of the corpus or corpora to identify other instances where similar patient attributes, medical condition attributes, and treatment attributes may be found to identify additional information to be ingested. For example, such searches may be keyed to the medical condition such that references to the medical condition may be initially found in other documents of the corpus or corpora, and then the content associated with instances of references to the medical condition may be searched to determine if any of the patient attributes, medical condition attributes, and/or treatment attributes, extracted from the positional statement in the medical treatment guideline document that was ingested, are mentioned in the content of these other documents that reference the medical condition.

For example, a corpus of documents may be searched for instances of "Type 2 Diabetes" in documents of the corpus. A subset of documents that comprise instances of references to the medical condition "Type 2 Diabetes" may then be searched for instances of clinical attributes being mentioned. These instances of clinical attributes may then be correlated with attributes of insight data structures of the medical condition base cartridge. Based on the cross-correlation of instances of references to attributes in association with the medical condition and/or treatment, documents in the corpus providing supporting evidence for the accuracy of the relationships between clinical attributes, treatments, and medical condition in the insight data structures may be identified and linked with the insight data structures.

In some illustrative embodiments, statistical measures regarding the occurrences or instances of the clinical attributes across the ingested medical treatment guidelines document, as well as other documents and sources of information in the corpus or corpora identified through cross-correlation, may be generated. For example, counts of instances of each clinical attribute may be generated and used to calculate these statistical measures, such as distributions, frequency of occurrence, inverse document frequency (IDF), etc. These statistical measures may be used to identify clinical attributes that are of relative greater importance than others in the evaluation of the insight data structures associated with the medical condition. For example, corresponding weight values (also simply referred to as weights) may be associated with these clinical attributes based on the relative importance in the insight data structures.

Thus, for example, it may be determined that the age of the patient is mentioned more often in documents of the corpus in relation to a medical condition and a particular treatment. As a result, age may be given a greater weight in the insight data structures corresponding to the medical condition and treatment as age appears, based on its frequency of occurrence in the documentation, to be a principle factor in determining the appropriateness of the mentioned treatment. Moreover, age may be more often associated with the medical condition as a whole, both with the particular treatment and with other treatments, which indicates that age is likewise more of a factor in determining what treatments are appropriate for treating the medical condition. In some cases, while age may be mentioned often in the context of references to the medical condition, it may be relatively less often mentioned in association with a given treatment option, in which case age may be given a relatively lower weight with regard to that particular treatment but a relatively higher weight with regard to other treatment options for the medical condition.

Alternatively, in some implementations, IDF may be more indicative of clinical attributes that are of relatively greater importance when evaluating insight data structures. For example, if a clinical attribute is mentioned relatively less often than other clinical attributes in association with the medical condition, but is mentioned in association with the treatment, then this may be indicative of the fact that this clinical attribute is a key attribute for determining the appropriateness of the treatment for treating the medical condition. Any suitable statistical measure, depending on the particular implementation, may be used to generate weight values that are used to relatively weight the clinical attributes of an insight data structure, without departing from the spirit and scope of the illustrative embodiments.

The weights associated with clinical attributes may be further influenced by the types of references to the clinical attributes presented in the positional statements, documents, or other information of a corpus or corpora. For example, analysis of the instances of clinical attribute references in statements, documents, or other information of the corpus or corpora may analyze the natural language content in proximity to the instance to determine whether the reference is a contraindication, a warning, an affirmation of the importance of the clinical attribute to the medical condition, or the like. For example, relatively lower weights are given to clinical attributes associated with the contraindication and higher weights are given to clinical attributes associated with warnings, with additionally higher weights associated with clinical attributes that do not fall within contraindications or warnings. Natural language processing techniques may be used to identify features within the natural language surrounding instances of clinical attribute references in statements, documents, or other information of the corpus or corpora to determine the types of references, e.g., key words, phrases, or language patterns may be identified that are correlated with contraindications, warnings, supportive references, etc.

In addition, weight values may be modified based on correlation of the clinical attributes with patient cohorts for the particular medical condition. That is, instances of clinical attribute references that are found from the natural language of the positional statement, document, or other corpus information may be cross-correlated with clinical attributes of patients falling into a patient cohort for the particular medical condition (e.g., group of patients that all suffer from the same medical condition, such as "Type 2 Diabetes" patients). The patient electronic health records (EHR) of the patients of a cohort are analyzed to identify occurrences of the same clinical attributes in the EHRs. More frequently occurring instances of the clinical attributes in the EHRs are then given relatively larger weight values. The highest weighted clinical attributes (higher than a predetermined threshold) are considered primary positive attributes in support of a treatment corresponding to the insight data structure of the medical condition base cartridge that is being processed or built. Similarly, lowest weighted clinical attributes or clinical attributes specifically associated with contraindication statements or warnings may be considered primary negative attributes contrary to treatment.

In some illustrative embodiments, the weight values associated with clinical attributes may be further determined based on grading values (or "gradings") associated with the positional statements from which these clinical attributes are obtained. That is, the positional statement in a guideline document may be given an associated grading by an oversight organization, such as a professional association, a government agency, or the like. For example, with regard to diabetes treatment guidelines and positional statements, the American Diabetes Association (ADA) may assign gradings to positional statements in accordance with their established grading policies, where the gradings indication a level of reliability of the knowledge presented in the corresponding positional statement. As an example, the ADA may assign gradings of A, B, C, or E to a positional statement that indicates a level of evidential support for the positional statement and thus, the reliability of the knowledge presented in the positional statement as such:

Grading A—Clear evidence from well-conducted, generalizable randomized controlled trials that are adequately powered, including:

1. Evidence from a well-conducted multicenter trial;
2. Evidence from a meta-analysis that incorporated quality ratings in the analysis;
3. Compelling non-experimental evidence, i.e. "all or none" rule developed by the Centre for Evidence-Based Medicine at the University of Oxford;
4. Supportive evidence from well-conducted randomized controlled trials that are adequately powered, including:
   evidence from a well-conducted trial at one or more institutions;
   evidence from a meta-analysis that incorporated quality ratings in the analysis.

Grading B—Supportive evidence from well-conducted cohort studies, including:

1. Evidence from a well-conducted prospective cohort study or registry;
2. Evidence from a well-conducted meta-analysis of cohort studies; and
3. Supportive evidence from a well-conducted case-control study.

Grading C—Supportive evidence from poorly controlled or uncontrolled studies, including:

1. Evidence from randomized clinical trials with one or more major, or three or more minor, methodology flaws that could invalidate the results;
2. Evidence from observational studies with high potential for bias (such as case series with comparison to historical controls);
3. Evidence from case series or case reports;
4. Conflicting evidence with the weight of evidence supporting the recommendation.

Grading E—Expert consensus of clinical experience.

The grading value information of a positional statement may be specified either as part of the natural language content of the medical treatment guidelines document, such as in association with the positional statement, or in metadata associated with the guidelines document and/or positional statement. This grading information may be extracted by the natural language processing performed on the positional statement when generating the medical condition base cartridge for a medical condition, e.g., Type 2 Diabetes base cartridge, or through analysis of metadata associated with the medical treatment guidelines document and/or positional statement. The better the grading value associated with the positional statement, e.g., grade A is better than grade E on the scale from A to E above, the greater the weight that is associated with the clinical attributes, treatment information, drug information, and other elements of the corresponding insight data structure present in the medical condition base cartridge that is obtained from the positional statement. Thus, the higher weighting based on grading will tend to make treatments associated with higher graded positional statements rank higher when performing cognitive operations by a cognitive system, such as in the generation of treatment recommendations by a cognitive treatment recommendation system for example, barring any identified contraindications. The positional statement grading based weight values may be applied to clinical attributes of the insight data structure either alone or in combination with one or more of the other weights discussed above.

The set of primary clinical attributes (both positive and negative), treatment information, which may include pharmaceutical information, and the weighting values, generated from positional statement, document, or other corpus information occurrences are aggregated to generate insight data structures of a base cartridge for the medical condition. The weight values may be determined, at least in part, by the grading of the positional statements as noted above. Thus, in addition to the clinical attribute information extracted from the positional statement itself, e.g., the insight data structure elements extracted from the positional statement in the example above being {medical condition=Type 2 diabetes, symptom=persistent rash, gender=female, age>=50, treatment=drug Z, dosage=1 pill per day}, the insight data structure may be extended to include pharmaceutical information for the treatment, e.g., warnings, contraindications, drug interaction information, etc., as extracted from pharmaceutical information sources of the corpus or corpora. For example, in addition to the elements above, the insight data structure may comprise elements of "drug interaction=drug X", "activity restriction=no heavy machinery", etc.

Moreover, the insight data structure may comprise weight values associated with primary and secondary clinical attributes as identified through cross-correlation with the medical treatment guidelines document, other documents in the corpus, patient cohorts for the medical condition, grading of positional statements, and the like. Thus, in addition to each of the clinical elements set forth above in the insight data structure, a weight value may be associated with the clinical elements as calculated based on an analysis of cross-correlations, e.g., "gender=female, 30" meaning that a 30% weighting factor is applied to this clinical attribute when performing a cognitive operation based on the combination of medical condition and treatment specified in the insight data structure. That is, if the cognitive medical system is a treatment recommendation system, then a 30% weighting is applied to the gender clinical attribute when evaluating the appropriateness of the treatment for the patient's medical condition corresponding to the insight data structure of the medical condition base cartridge. The weight value, or weighting factor, may be a single value that is derived based on one or more of the cross-correlation, patient cohort analysis, positional statement grading values, and the like. Alternatively, a plurality of weighting values may be associated with each the clinical attributes, each weighting value being generated based on a different analysis, e.g., a cross-correlation based weighting value, patient cohort based weighting value, positional statement grading based weighting value, etc.

The process for building a medical condition base cartridge as discussed above can be performed repeatedly for each positional statement of each document, e.g., each medical treatment guideline document, ingested such that one or more insight data structures are generated for one or more medical condition base cartridges. For example, multiple positional statements associated with different treatments for Type 2 Diabetes may be ingested and processed in the manner described above to generate a plurality of insight data structures that are compiled into a medical condition base cartridge for Type 2 Diabetes. Thus, the medical condition base cartridge stores the insight data structures that identify the clinical attributes, pharmaceutical information, cross-correlation based weighting values, patient cohort based weighting values, positional statement grading based weighting values, and the like, relevant to a plurality of treatments for the medical condition corresponding to the medical condition base cartridge, e.g., a plurality of treatments for Type 2 Diabetes in the running example.

The medical condition base cartridge, which is automatically generated using the cognitive process described above, may then be used as a ground truth for training a cognitive medical system to perform its cognitive operations through a machine learning process with the medical condition base cartridge providing the insight data structures for a medical condition that may be processed or otherwise implemented by the cognitive medical system. For example, in an implementation where the cognitive medical system is a cognitive medical treatment recommendation system, the medical condition base cartridge may be used to provide the insight data structures that are applied by the cognitive medical treatment recommendation system to patient electronic medical record (EMR) data to determine if particular medical treatments are appropriate for the patient. Thus, for example, if the patient is diagnosed with Type 2 Diabetes, the corresponding Type 2 Diabetes base cartridge may be plugged into, and loaded by, the cognitive medical treatment recommendation system and test data representing one or more patient EMRs may be evaluated using the insight data structures present in the Type 2 Diabetes base cartridge. For example, for a plurality of treatments having insight data structures in the Type 2 Diabetes base cartridge, the clinical attributes present in the patient EMRs are evaluated against the clinical attributes specified in the insight data structure, utilizing the corresponding weighting values if any, to generate a score indicative of the appropriateness of the corresponding treatment for the particular patient and patient medical condition. The treatments may then be ranked and a final treatment recommendation selected. This final treatment recommendation may be compared against a known correct treatment recommendation to determine if the cognitive medical treatment recommendation system is generating correct results and if not, the operation of the cognitive medical treatment recommendation system may be modified to adjust the operation to approach generating the correct result.

In addition to training, the medical condition base cartridge may be used during runtime analysis of patient EMRs to perform cognitive medical system operations. For example, in a cognitive medical treatment recommendation system, the cognitive medical treatment recommendation system may evaluate the various treatments for a medical condition of a patient being evaluated, based on the corresponding medical condition base cartridge for the medical condition, so as to determine which treatment to recommend. Thus, the medical condition base cartridge may be used both for training purposes and for runtime analysis of patient information.

It should be appreciated that multiple medical condition base cartridges may be automatically generated through the above cognitive processes, and stored in a medical condition base cartridge storage or repository. Thus, the cognitive medical system may be dynamically configured through the plugging in and loading of medical condition base cartridges. For example, in response to a determination of a medical condition of a patient, the corresponding medical condition base cartridge(s) may be selected from the storage, plugged into the logic of the cognitive medical system, loaded and applied to the patient information to perform a cognitive medical operation.

In some illustrative embodiments, the cognitive medical system provides a general pluggable framework for the medical condition base cartridges. An example of such a framework is described in commonly assigned and U.S. patent application Ser. No. 15/262,311. As described in this co-pending application, the cognitive medical system is trained independent of any particular medical condition and utilizes medical condition independent scoring features to evaluate treatment recommendations. The medical condition specific scoring features are specified in medical condition specific cartridges. In a similar manner, the medical condition base cartridges of the present illustrative embodiments may provide medical condition specific insight data structures which provide the information for evaluating clinical attributes, applying weightings indicative of the relative importance of clinical attributes to determining the applicability of a treatment to particular types of patients, and scoring the treatments for applicability to particular patient clinical attributes. Thus, similar to the co-pending application, medical condition specific scoring features are provided in the medical condition base cartridge and may be used to customize the operation of the cognitive medical system to particular medical conditions.

Thus, the illustrative embodiments provide mechanisms in which cognitive techniques, e.g., structured and/or non-structured content analysis logic, such as natural language processing logic, are provided to extract and/or derive a set of insight data structures from natural language content, such as positional statements in medical treatment guideline documents and other types of medical condition treatment documentation in a corpus or corpora, for each medical treatment in a plurality of medical treatments associated with each medical condition in a plurality of medical conditions. This extracted/derived set of insight data structures may be used to generate one or more medical condition base cartridges that are each specific to a medical condition and provide the logic/criteria for performing medical condition specific evaluation of treatments for the corresponding medical condition. The resulting medical condition base cartridges may then be used to train the cognitive medical system and/or perform runtime cognitive medical operations on patient information.

Figure 2:
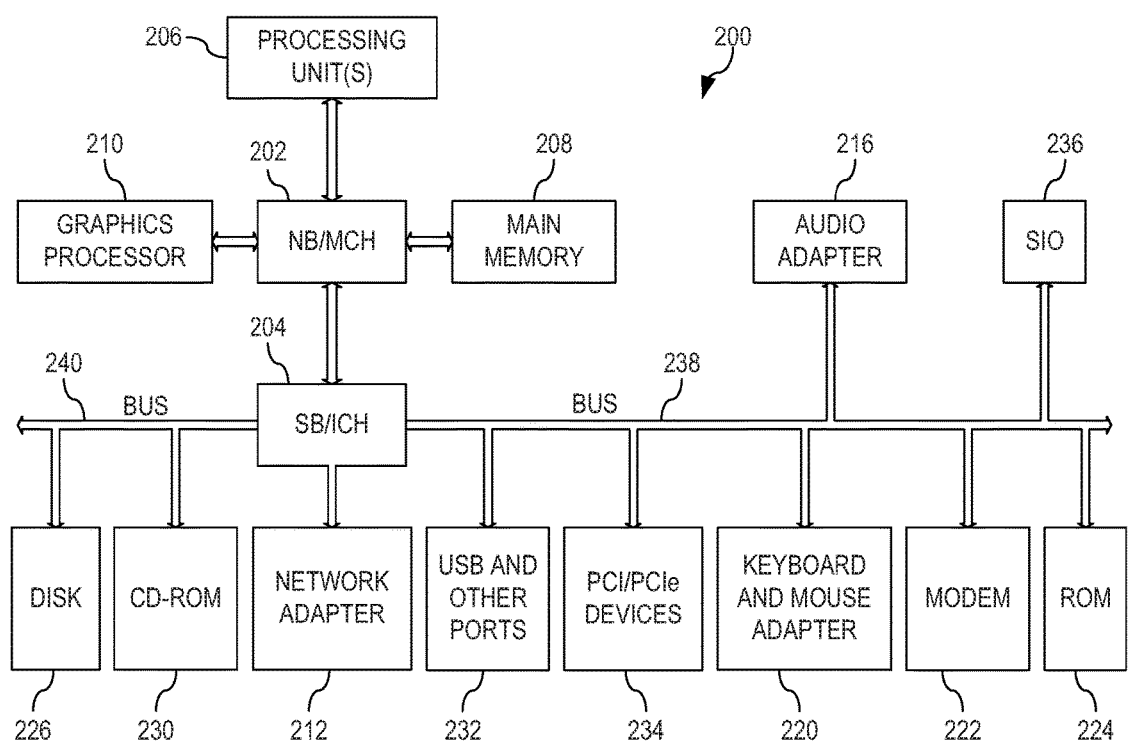
FIG. 2 is a block diagram of an example data processing system in which aspects of the illustrative embodiments are implemented.
Figure 3:
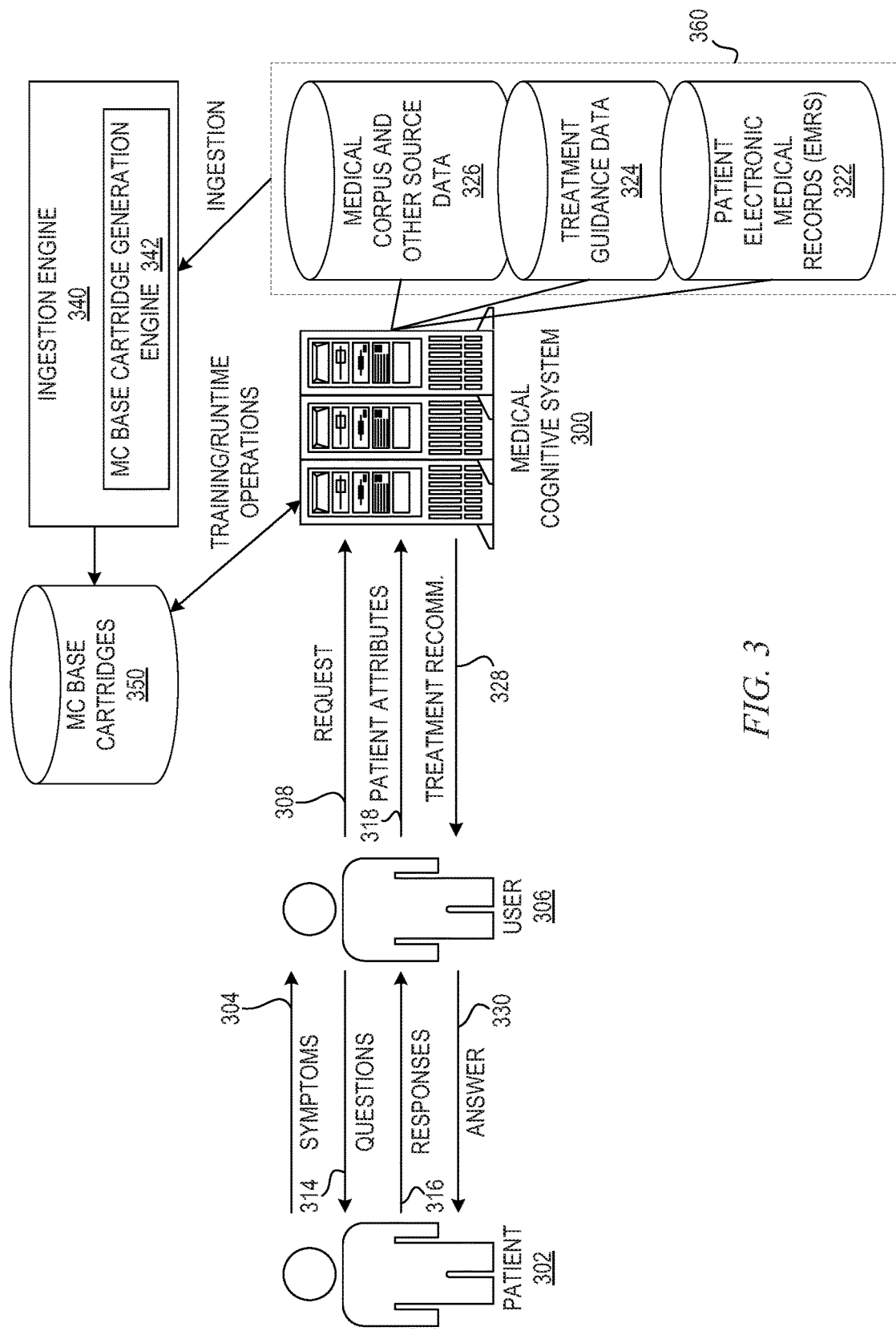
FIG. 3 is an example diagram illustrating an interaction of elements of a cognitive medical system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-4 are directed to describing an example cognitive system, such as cognitive system 100 in FIG. 1, for healthcare applications (also referred to herein as a "cognitive medical system") which implements a request processing pipeline (e.g., 108 in FIG. 1), such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the cognitive medical system. As described in more detail hereafter, the particular healthcare application that is implemented in the cognitive system of the present invention is a healthcare application for providing medical treatment recommendations for patients based on their specific features as obtained from various sources, e.g., patient electronic medical records (EMRs), patient questionnaires, medical lab reports, medical insurance claims information, etc. While a medical treatment recommendation system will be used as an example, the illustrative embodiments are not limited to such and may be used with any decision support system, cognitive processing system, or the like.

In particular, the mechanisms of the present invention provide mechanisms for automatically generating one or more medical condition base cartridges using cognitive analysis of structured and/or unstructured content of one or more corpora. The mechanisms of the illustrative embodiments may further provide for the training of a cognitive medical system, such as the cognitive medical treatment recommendation system, to perform a cognitive medical operation based on the insight data structures present in the medical condition base cartridges. This training may utilize the medical condition base cartridges and training sets of patient information and expected treatment recommendation results to train the cognitive medical treatment recommendation system to provide the expected treatment recommendation results and then use the trained logic to operate on new patient information during runtime analysis. Furthermore, the mechanisms of the illustrative embodiments may provide for the utilization of such medical condition base cartridges to perform runtime cognitive medical operations, e.g., generating treatment recommendations for identified medical conditions of patients based on the application of insight data structures in the medical condition base cartridges to the patient information.

It should be appreciated that the cognitive medical system, while shown in FIGS. 1-4 as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical condition domain (e.g., various types of blood diseases) while another request processing pipeline may be trained to answer input requests in another medical condition domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc. Thus, in the context of the illustrative embodiments, each pipeline may have a separate set of medical condition base cartridges upon which it is trained, and with which it operates to process patient information.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The cognitive medical system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?", the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of the QA pipeline, or request processing pipeline, mechanisms of a cognitive medical system such that they are trained and/or operate based on medical condition base cartridges which set forth the insight data structures that provide structured representations of knowledge about a corresponding medical condition and its treatments. The medical condition base cartridges are generated automatically through cognitive processes, as discussed above, to extract features indicative of the medical condition attributes, treatment attributes, and patient attributes, as well as any suitable weightings based on cross-correlations and analysis of types of references to attributes found in other documentation of a corpus or corpora, supporting evidence passage information for content present in the corpus or corpora that provide support for the knowledge present in the extracted features, patient cohort analysis, positional statement grading values, and the like. The extracted features, weightings, supporting evidence passage information, and the like, may be compiled into insight data structures stored in one or more medical condition base cartridges which are maintained in a medical condition base cartridge repository. Based on an identified medical condition of a patient, a corresponding medical condition base cartridge may be retrieved from the repository, loaded into the cognitive medical system, and used as a basis to evaluate potential treatments for the medical condition.

Since the illustrative embodiments may be implemented such that they extend the capabilities of cognitive systems and, in some illustrative embodiments a QA system pipeline, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-4 are only examples and are not intended to state or imply any limitation with regard to the type of cognitive system mechanisms with which the illustrative embodiments are implemented. Many modifications to the example cognitive system shown in FIGS. 1-4 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

- Navigate the complexities of human language and understanding
- Ingest and process vast amounts of structured and unstructured data
- Generate and evaluate hypothesis
- Weigh and evaluate responses that are based only on relevant evidence
- Provide situation-specific advice, insights, and guidance
- Improve knowledge and learn with each iteration and interaction through machine learning processes
- Enable decision making at the point of impact (contextual guidance)
- Scale in proportion to the task
- Extend and magnify human expertise and cognition
- Identify resonating, human-like attributes and traits from natural language
- Deduce various language specific or agnostic attributes from natural language
- High degree of relevant recollection from data points (images, text, voice) (memorization and recall)
- Predict and sense with situational awareness that mimic human cognition based on experiences
- Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The cognitive system 100 and network 102 enables question processing and answer generation (QA) functionality for one or more cognitive system users via their respective computing devices 110-112. Other embodiments of the cognitive system 100 may be used with components, systems, subsystems, and/or devices other than those that are depicted herein.

The cognitive system 100 is configured to implement a QA pipeline 108 that receive inputs from various sources. For example, the cognitive system 100 receives input from the network 102, a corpus of electronic document data 130, cognitive system users, and/or other data and other possible sources of input. In one embodiment, some or all of the inputs to the cognitive system 100 are routed through the network 102. The various computing devices 104 on the network 102 include access points for content creators and QA system users. Some of the computing devices 104 include devices for a database storing a corpus of data 106 (which is shown as a separate entity in FIG. 1 for illustrative purposes only). Portions of the corpus of electronic document data 130 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus of electronic document data 130 for use as part of a corpus with the cognitive system 100. The document includes any file, text, article, or source of data for use in the cognitive system 100. QA system users access the cognitive system 100 via a network connection or an Internet connection to the network 102, and input questions to the cognitive system 100 that are answered by the content in the corpus of electronic document data 130. In one embodiment, the questions are formed using natural language. The cognitive system 100 parses and interprets the question via a QA pipeline 108, and provides a response to the cognitive system user, e.g., cognitive system user 110, containing one or more answers to the question. In some embodiments, the cognitive system 100 provides a response to users in a ranked list of candidate answers while in other illustrative embodiments, the cognitive system 100 provides a single final answer or a combination of a final answer and ranked listing of other candidate answers.

The cognitive system 100 implements the QA pipeline 108 which comprises a plurality of stages for processing an input question and the corpus of electronic document data 130. The QA pipeline 108 generates answers for the input question based on the processing of the input question and the corpus 130. The QA pipeline 108 will be described in greater detail hereafter with regard to FIG. 3.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a QA pipeline of the IBM Watson™ cognitive system receives an input question which it then parses to extract the major features of the question, which in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The QA pipeline of the IBM Watson™ cognitive system then performs deep analysis on the language of the input question and the language used in each of the portions of the corpus of data found during the application of the queries using a variety of reasoning algorithms.

The scores obtained from the various reasoning algorithms are then weighted against a statistical model that summarizes a level of confidence that the QA pipeline of the IBM Watson™ cognitive system has regarding the evidence that the potential response, i.e. candidate answer, is inferred by the question. This process is be repeated for each of the candidate answers to generate ranked listing of candidate answers which may then be presented to the user that submitted the input question, or from which a final answer is selected and presented to the user. More information about the QA pipeline of the IBM Watson™ cognitive system may be obtained, for example, from the IBM Corporation website, IBM Redbooks, and the like. For example, information about the QA pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based cognitive operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, various other types of medical decision support operations, or the like. Thus, the cognitive system 100 may be a cognitive medical system 100 that operates in the medical or healthcare type domains and which may process requests for such healthcare operations via the request processing pipeline 108 input as either structured or unstructured requests, natural language input questions, or the like.

In one illustrative embodiment, the cognitive system 100 is a medical treatment recommendation system that analyzes a patient's EMR in relation to medical guidelines and other medical documentation in a corpus of information, to generate a recommendation as to how to treat a medical condition of the patient. In particular, the cognitive system 100 implements a pluggable framework in which medical condition base cartridges are plugged into the framework to provide insight data structures defining, in a structured manner, the treatments for specific medical conditions and the corresponding clinical attributes and other medical knowledge extracted from natural language content of a corpus or corpora of electronic documents 130. The cognitive system 100 may be trained using such medical condition base cartridges and may further perform runtime operations using the knowledge represented in the insight data structures of such medical condition base cartridges.

As shown in FIG. 1, the cognitive system 100 is augmented, in accordance with the mechanisms of the illustrative embodiments, to include logic implemented in specialized hardware, software executed on hardware, or any combination of specialized hardware and software executed on hardware, for implementing an ingestion engine 120 having a medical condition (MC) base cartridge generation engine 122. It should be appreciated that while the ingestion engine 120 and MC base cartridge generation engine 122 are shown in FIG. 1 as separate entities from that of the cognitive system 100, the illustrative embodiments are not limited to such. Rather, the elements of the ingestion engine 120 and/or MC base cartridge generation engine 122 may be integrated into the cognitive system 100 and various elements or logic of the ingestion engine 120 and/or MC base cartridge generation engine 122 may be integrated in, or otherwise operate in conjunction with, various logic stages of the request processing pipeline 108.

As shown in FIG. 1, the MC base cartridge engine 122 comprises positional statement feature extraction engine 124, cross-correlation engine 126, and insight data structure generation engine 128. In general, any functionality or operations described herein that are not specifically attributed to one of the elements 124-128 may be implemented in other logic of the ingestion engine 120 and/or MC base cartridge generation engine 122 including, but not limited to, control logic for controlling the operations of the elements 124-128 and orchestrating their interactions, configuration, and implementation.

It should be noted that in this example, it is assumed that the MC base cartridge engine 122 operates on positional statements in medical treatment guideline documents of a corpus 130, however the illustrative embodiments are not limited to such. Rather, the illustrative embodiments may ingest and operate on any portion of natural language content from the corpus 130 which may comprise information regarding a medical condition and one or more treatments associated with the medical condition.

The ingestion engine 120, among other ingestion operations for generating in-memory representations of the information present in content present in the corpus or corpora 130, performs operations for generating one or more medical condition (MC) base cartridges via the MC base cartridge generation engine 122. With the mechanisms of the illustrative embodiments, as part of the MC base cartridge generation operation, in response to a positional statement being encountered in a document, such as a medical treatment guideline document in the corpus 130, the positional statement feature extraction engine 124 operates to extract the recognizable features from the positional statement. Such features may include the medical condition name or other identifier that the positional statement references, the treatment name or identifier that the positional statement references, as well as medical condition attributes, treatment attributes, and patient attributes (again, collectively referred to herein as "clinical attributes"). Based on this extraction of features, a set of correlated information for a combination of medical condition, treatment, and clinical attributes is generated, sometimes referred to herein as an initial insight data structure, which is then used as a basis for building a final insight data structure for the positional statement.

The initial insight data structure is provided to the cross-correlation engine 126 which performs cross-correlation operations for the various features and clinical attributes in the initial insight data structure with regard to documents within the corpus or corpora 130. As discussed above, this cross-correlation operation may comprise identifying instances of references to the medical condition in documents to thereby generate a subset of documents from the corpus that reference the medical condition. Of this first subset, a second subset may be identified by identifying documents within the first subset that also reference the treatment of the initial insight data structure. Both the first subset and the second subset may be further analyzed to identify references to other features and clinical attributes specified in the initial insight data structure, to thereby generate statistical measures and links to supporting evidential passages. Furthermore, the cross-correlation engine 126 may identify types of references to the various features of the initial insight data structure based on cognitive natural language processing of the surrounding text of the references to identify the nature of the reference, e.g., contraindication, warning, supporting evidence, etc.

Based on the evaluation of the cross-correlations, the cross-correlation engine 126 may generate weighting values to be applied to one or more of the features present in the initial insight data structure. As noted above, these weighting values may be modified or adjusted based on further analysis of patient cohort evaluations, positional statement gradings, and the like. These weighting values, or modified/adjusted weighting values, as well as links to the supporting evidence passages, are provided to the insight data structure generation engine 128 which combines this information with the initial insight data structure to generate a final insight data structure for the positional statement. The insight data structure generation engine 128 stores the final insight data structure as part of the medical condition (MC) base cartridge for the medical condition specified in the positional statement.

It should be appreciated that this process may be repeated for each subsequent positional statement ingested by the ingestion engine 120 and processed by the MC base cartridge generation engine 122. As such, the MC base cartridge generation engine 122 may, based on identification of the medical condition through the feature extraction performed by the positional statement feature extraction engine 124, may perform a lookup in the medical condition cartridge repository 140 to determine if a MC base cartridge 142 for the medical condition already exists in the repository 140. If one already exists, then the corresponding MC base cartridge 142 may be retrieved and updated with an additional entry corresponding to the final insight data structure generated for the positional statement being processed. If one does not already exist, a new MC base cartridge 142 may be generated.

It should be appreciated that MC base cartridges 142 may be periodically invalidated such that they are rebuilt and thereby comprise the most up-to-date knowledge for the medical condition. Alternatively, each individual entry in the MC base cartridge may have an associated timestamp when it was created or last updated so as to invalidate stale entries so that they may be rebuilt at a later time. In such a case, the entries may have links to positional statements that are the foundation of the insight data structure corresponding to the entry so that this positional statement may be reprocessed through the ingestion engine 120 when the entry is determined to be stale, i.e. older than a predetermined threshold period of time.

The MC base cartridges 142 of the repository 140 may be used to train the cognitive system 100 and/or request processing pipeline 108 of the cognitive system 100 in the manner previously described above, or any other suitable training methodology for the particular implementation. The cognitive system 100 provides a pluggable framework in which the MC base cartridges 142 may be plugged into and loaded by the framework such that the cognitive system 100 is then configured to perform cognitive operations with regard to the specific medical conditions corresponding to the plugged-in and loaded MC base cartridges 142. The cognitive system 100 may then be trained using training sets of patient information and desired cognitive operation results, e.g., output treatment recommendations, so as to tune the weighting values, scoring logic, or any other analysis or evaluation logic implemented by the cognitive system 100 to perform the cognitive operation.

In addition, the MC base cartridges 142 may be plugged into and loaded by the cognitive system 100 during runtime operation so as to configure the cognitive system 100 for performing cognitive operations with regard to the corresponding medical conditions. For example, in some illustrative embodiments, the cognitive system 100 may process an input request/question identifying a particular patient and medical condition. The identity of the medical condition may be used to send a request to the MC base cartridge repository 140 to retrieve and plug-in/load a corresponding MC base cartridge 142 for the medical condition. In this way, the cognitive system 100 is then specifically configured to operate with regard to the medical condition specified in the request/question. The cognitive system 100 and/or request processing pipeline 108 may then apply the knowledge represented in the insight data structures of the MC base cartridge 142 to the patient information for the identified patient to thereby evaluate the various possible treatments for the patient's medical condition with regard to the cognitive operation being performed by the cognitive system 100.

Thus, the illustrative embodiments provide mechanisms for automatically and cognitively generating a medical condition base cartridge which can be used as a basis for training a cognitive system. Moreover, the illustrative embodiments provide mechanisms for providing medical condition base cartridges for use by a cognitive system when performing runtime cognitive operations on patient information.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE)

or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System P® computer system, running the Advanced Interactive Executive) (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a cognitive medical system in accordance with one illustrative embodiment. The example diagram of FIG. 3 depicts an implementation of a cognitive medical system 300 that is configured to provide medical treatment recommendations for patients. However, it should be appreciated that this is only an example implementation and other cognitive medical or healthcare based operations may be implemented in other embodiments of the cognitive medical system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the cognitive medical system 300 as patient attributes 318. Interactions between the user 306 and the cognitive medical system 300 will be electronic via a user computing device (not shown), such as a client computing device 110 or 112 in FIG. 1, communicating with the cognitive medical system 300 via one or more data communication links and potentially one or more data networks.

As shown in FIG. 3, in accordance with one illustrative embodiment, a patient 302 presents symptoms 304 of a medical condition to a user 306, such as a healthcare practitioner (doctor, nurse, nurse practitioner, etc.), technician, or the like. The user 306 may interact with the patient 302 via a question 314 and response 316 exchange where the user 306 gathers more information about the patient 302, the symptoms 304, and the medical condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases such medical equipment may be medical equipment typically used in hospitals or medical centers to monitor vital signs and medical conditions of patients that are present in hospital beds for observation or medical treatment.

In response, the user 302 submits a request 308 to the cognitive medical system 300, such as via a user interface on a client computing device that is configured to allow users to submit requests to the cognitive medical system 300 in a format that the cognitive medical system 300 can parse and process. The request 308 may include, or be accompanied with, information identifying patient attributes 318. These patient attributes 318 may include, for example, an identifier of the patient 302 which may be used to retrieve patient EMRs 322 for the patient, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the cognitive medical system 300 may be included in the request 308 and/or patient attributes 318.

The cognitive medical system 300 provides a cognitive system that is specifically configured to perform an implementation specific medical or healthcare oriented cognitive operation. In the depicted example, this medical or healthcare oriented cognitive operation is directed to providing a treatment recommendation 328 to the user 306 to assist the user 306 in treating the patient 302 based on their reported symptoms 304 and other information gathered about the patient 302 via the question 314 and response 316 process and/or medical equipment monitoring/data gathering. The cognitive medical system 300 operates on the request 308 and patient attributes 318 utilizing information gathered from the medical corpus and other source data 326, treatment guidance data 324, and the patient EMRs 322 associated with the patient 302 to generate one or more treatment recommendation 328. The treatment recommendations 328 may be presented in a ranked ordering with associated supporting evidence, obtained from the patient attributes 318 and data sources 322-326, indicating the reasoning as to why the treatment recommendation 328 is being provided and why it is ranked in the manner that it is ranked.

For example, based on the request 308 and the patient attributes 318, the cognitive medical system 300 may operate on the request, such as by using a QA pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve candidate treatment recommendations (or answers to the input question), and score these candidate treatment recommendations based on supporting evidence found in the data sources 322-326.

In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients, such as patient 302, in a manner (structured, unstructured, or a mix of structured and unstructured formats) that the information may be retrieved and processed by the cognitive medical system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the cognitive medical system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the cognitive medical system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical condition/condition. For example, the treatment guidance data 324 may comprise a treatment recommendation rule that indicates that for a treatment of Decitabine, strict criteria for the use of such a treatment is that the patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs indicating evidence of cardiac disease, the following conditions of the treatment rule exist:

Age<=60 years=59 (MET);
Patient has AML=AML (MET); and
Cardiac Disease=false (MET)

Since all of the criteria of the treatment rule are met by the specific information about this patient 302, then the treatment of Decitabine is a candidate treatment for consideration for this patient 302. However, if the patient had been 69 years old, the first criterion would not have been met and the Decitabine treatment would not be a candidate treatment for consideration for this patient 302. Various potential treatment recommendations may be evaluated by the cognitive medical system 300 based on ingested treatment guidance data 324 to identify subsets of candidate treatments for further consideration by the cognitive medical system 300 by scoring such candidate treatments based on evidential data obtained from the patient EMRs 322 and medical corpus and other source data 326.

For example, data mining processes may be employed to mine the data in sources 322 and 326 to identify evidential data supporting and/or refuting the applicability of the candidate treatments to the particular patient 302 as characterized by the patient's patient attributes 318 and EMRs 322. For example, for each of the criteria of the treatment rule, the results of the data mining provides a set of evidence that supports giving the treatment in the cases where the criterion is "MET" and in cases where the criterion is "NOT MET." The cognitive medical system 300 processes the evidence in accordance with various cognitive logic algorithms to generate a confidence score for each candidate treatment recommendation indicating a confidence that the corresponding candidate treatment recommendation is valid for the patient 302. The candidate treatment recommendations may then be ranked according to their confidence scores and presented to the user 306 as a ranked listing of treatment recommendations 328. In some cases, only a highest ranked, or final answer, is returned as the treatment recommendation 328. The treatment recommendation 328 may be presented to the user 306 in a manner that the underlying evidence evaluated by the cognitive medical system 300 may be accessible, such as via a drilldown interface, so that the user 306 may identify the reasons why the treatment recommendation 328 is being provided by the cognitive medical system 300.

In accordance with the illustrative embodiments herein, the cognitive medical system 300 is augmented to operate with, implement, or include medical condition (MC) base cartridges repository 350 which stores MC base cartridges generated by the MC base cartridge generation engine 342 of the ingestion engine 340. The MC base cartridge generation engine 342 of the ingestion engine 340 may operate in the manner as previously described above with regard to one or more of the illustrative embodiments. The resulting MC base cartridges stored in the repository 350 may be provided to the medical cognitive system 300 for training and/or runtime evaluation of patient information. For example, with regard to runtime operation, in the above description where the treatment guidance data 324 is described as being used by the medical cognitive system 300 to evaluate patient information to generate treatment recommendations, the medical cognitive system 300 may utilize the MC base cartridge for the medical condition of the patient 302 to provide insight data structures that define the rules, e.g., a logical combination of clinical attributes and weighting values, that are applied by the medical cognitive system 300 to the patient attributes 318 to determine the applicability of various treatments of the medical condition for this particular patient 302. With regard to training, the training may be performed in any suitable manner, such as the methodology previously described above.

Thus, in response to the cognitive medical system 300 receiving the request 308 and patient attributes 318, the cognitive medical system 300 may retrieve the patient's EMR data from source(s) 322. This information is provided to the medical cognitive system 300 which is configured with one or more medical condition (MC) specific cartridges 350 for one or more medical conditions and corresponding treatments for which the patient 302 is to be evaluated. In some illustrative embodiments, the request 308 may specify the types of medical conditions, class or classes of medical conditions, or domain(s) of medical conditions to be considered with regard to the specified patient, e.g., "what treatment should I prescribe to patient A for her diabetes?" indicates that the medical condition or medical class/domain is diabetes. If such specification is made in the request 308, then the corresponding MC cartridges 350 may be loaded or ingested so as to configure the medical cognitive system 300 operation for class(es) or domain(s) of the medical conditions corresponding to the specific request 308.

The patient attributes 318 and patient EMR information from source(s) 322 are input to the medical cognitive system 300 configured with the corresponding MC cartridges 350 which causes the patient attributes 318 and patient EMR information to be analyzed and scored, in accordance with the logical combinations of clinical attributes and weighting values specified in the insight data structures of the MC cartridges 350, to generate a confidence score for each treatment of a medical condition for which the patient 302 is being evaluated. The resulting confidence score for each potential treatment recommendation is further evaluated using logic of the request processing pipeline(s) implemented in the medical cognitive system 300 against other information in the medical corpus and other source data 326 and treatment guidance data 324 to generate final confidence scores for various treatment recommendations. The final confidence scores may then be ranked by the cognitive medical system 300 relative to one another and used to generate a final treatment recommendation 328, or categorized set of treatment recommendations, e.g., treatments may be categorized into various categories of confidence such as "recommended", "suggested", and "not recommended."

While FIG. 3 is depicted with an interaction between the patient 302 and a user 306, which may be a healthcare practitioner such as a physician, nurse, physician's assistant, lab technician, or any other healthcare worker, for example, the illustrative embodiments do not require such. Rather, the patient 302 may interact directly with the cognitive medical system 300 without having to go through an interaction with the user 306 and the user 306 may interact with the cognitive medical system 300 without having to interact with the patient 302. For example, in the first case, the patient 302 may be requesting 308 treatment recommendations 328 from the cognitive medical system 300 directly based on the symptoms 304 provided by the patient 302 to the cognitive medical system 300. Moreover, the cognitive medical system 300 may actually have logic for automatically posing questions 314 to the patient 302 and receiving responses 316 from the patient 302 to assist with data collection for generating treatment recommendations 328. In the latter case, the user 306 may operate based on only information previously gathered and present in the patient EMR 322 by sending a request 308 along with patient attributes 318 and obtaining treatment recommendations in response from the cognitive medical system 300. Thus, the depiction in FIG. 3 is only an example and should not be interpreted as requiring the particular interactions depicted when many modifications may be made without departing from the spirit and scope of the present invention.

As mentioned above, the cognitive medical system 300 may include a request processing pipeline, such as request processing pipeline 108 in FIG. 1, which may be implemented, in some illustrative embodiments, as a Question Answering (QA) pipeline. The QA pipeline may receive an input question, such as "what is the appropriate treatment for patient P?", or a request, such as "diagnose and provide a treatment recommendation for patient P."

Figure 4:
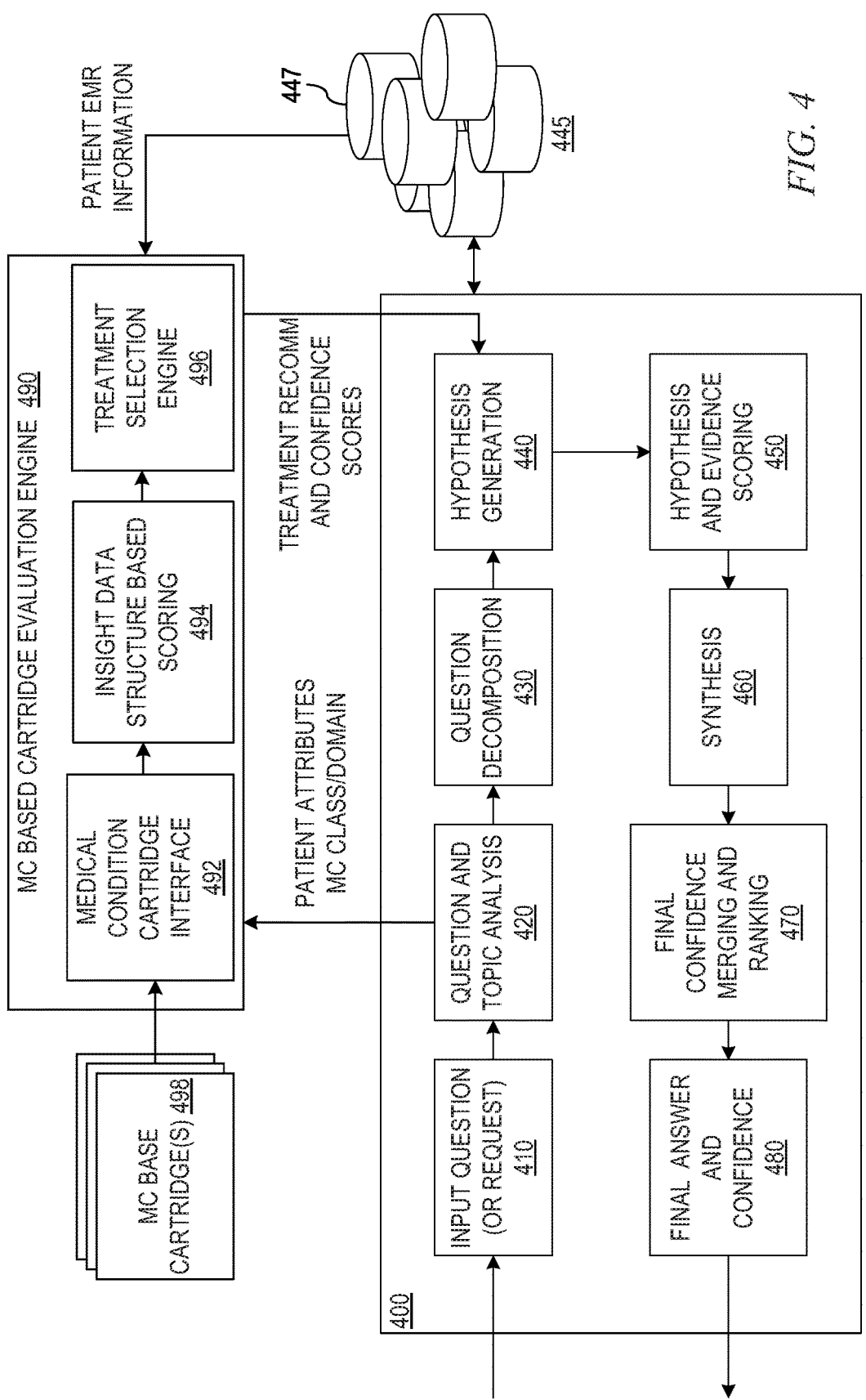
FIG. 4 illustrates a cognitive healthcare system implementing a Question and Answer (QA) or request processing pipeline for processing an input question or request in accordance with one illustrative embodiment.

FIG. 4 illustrates a QA pipeline of a cognitive medical system, such as cognitive medical system 300 in FIG. 3, or an implementation of cognitive system 100 in FIG. 1, for processing an input question in accordance with one illustrative embodiment. It should be appreciated that the stages of the QA pipeline shown in FIG. 4 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The QA pipeline of FIG. 4 is augmented, for example, in one or more of the stages to implement the improved mechanism of the illustrative embodiments described hereafter, additional stages may be provided to implement the improved mechanism, or separate logic from the pipeline 400 may be provided for interfacing with the pipeline 400 and implementing the improved functionality and operations of the illustrative embodiments.

As shown in FIG. 4, the QA pipeline 400 comprises a plurality of stages 410-480 through which the cognitive system operates to analyze an input question and generate a final response. In an initial question input stage 410, the QA pipeline 400 receives an input question that is presented in a natural language format. That is, a user inputs, via a user interface, an input question for which the user wishes to obtain an answer, e.g., "What medical treatments for diabetes are applicable to a 60 year old patient with cardiac disease?" In response to receiving the input question, the next stage of the QA pipeline 400, i.e. the question and topic analysis stage 420, parses the input question using natural language processing (NLP) techniques to extract major features from the input question, and classify the major features according to types, e.g., names, dates, or any of a plethora of other defined topics. For example, in a question of the type "Who were Washington's closest advisors?", the term "who" may be associated with a topic for "persons" indicating that the identity of a person is being sought, "Washington" may be identified as a proper name of a person with which the question is associated, "closest" may be identified as a word indicative of proximity or relationship, and "advisors" may be indicative of a noun or other language topic. Similarly, in the previous question "medical treatments" may be associated with pharmaceuticals, medical procedures, holistic treatments, or the like, "diabetes" identifies a particular medical condition, "60 years old" indicates an age of the patient, and "cardiac disease" indicates an existing medical condition of the patient.

In addition, the extracted major features include key words and phrases, classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500s to speed up the game and involves two pieces of the same color?," the LAT is the string "maneuver." The focus of a question is the part of the question that, if replaced by the answer, makes the question a standalone statement. For example, in the question "What drug has been shown to relieve the symptoms of ADD with relatively few side effects?," the focus is "drug" since if this word were replaced with the answer, e.g., the answer "Adderall" can be used to replace the term "drug" to generate the sentence "Adderall has been shown to relieve the symptoms of ADD with relatively few side effects." The focus often, but not always, contains the LAT. On the other hand, in many cases it is not possible to infer a meaningful LAT from the focus.

Referring again to FIG. 4, the identified major features are then used during the question decomposition stage 430 to decompose the question into one or more queries that are applied to the corpora of data/information 445 in order to generate one or more hypotheses. The queries are generated in any known or later developed query language, such as the Structure Query Language (SQL), or the like. The queries are applied to one or more databases storing information about the electronic texts, documents, articles, websites, and the like, that make up the corpora of data/information 445. That is, these various sources themselves, different collections of sources, and the like, represent a different corpus 447 within the corpora 445. There may be different corpora 447 defined for different collections of documents based on various criteria depending upon the particular implementation. For example, different corpora may be established for different topics, subject matter categories, sources of information, or the like. As one example, a first corpus may be associated with healthcare documents directed to cancer treatments while a second corpus may be associated with communicable disease treatments. Alternatively, one corpus may be documents published by the U.S. Department of Health and Human Services while another corpus may be American Medical Association documents. Any collection of content having some similar attribute may be considered to be a corpus 447 within the corpora 445.

The queries are applied to one or more databases storing information about the electronic texts, documents, articles, websites, and the like, that make up the corpus of data/information, e.g., the corpus of data 106 in FIG. 1. The queries are applied to the corpus of data/information at the hypothesis generation stage 440 to generate results identifying potential hypotheses for answering the input question, which can then be evaluated. That is, the application of the queries results in the extraction of portions of the corpus of data/information matching the criteria of the particular query. These portions of the corpus are then analyzed and used, during the hypothesis generation stage 440, to generate hypotheses for answering the input question. These hypotheses are also referred to herein as "candidate answers" for the input question. For any input question, at this stage 440, there may be hundreds of hypotheses or candidate answers generated that may need to be evaluated.

The QA pipeline 400, in stage 450, then performs a deep analysis and comparison of the language of the input question and the language of each hypothesis or "candidate answer," as well as performs evidence scoring to evaluate the likelihood that the particular hypothesis is a correct answer for the input question. As mentioned above, this involves using a plurality of reasoning algorithms, each performing a separate type of analysis of the language of the input question and/or content of the corpus that provides evidence in support of, or not in support of, the hypothesis. Each reasoning algorithm generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In generally, however, these algorithms look for particular terms, phrases, or patterns of text that are indicative of terms, phrases, or patterns of interest and determine a degree of matching with higher degrees of matching being given relatively higher scores than lower degrees of matching.

Thus, for example, an algorithm may be configured to look for the exact term from an input question or synonyms to that term in the input question, e.g., the exact term or synonyms for the term "movie," and generate a score based on a frequency of use of these exact terms or synonyms. In such a case, exact matches will be given the highest scores, while synonyms may be given lower scores based on a relative ranking of the synonyms as may be specified by a subject matter expert (person with knowledge of the particular domain and terminology used) or automatically determined from frequency of use of the synonym in the corpus corresponding to the domain. Thus, for example, an exact match of the term "movie" in content of the corpus (also referred to as evidence, or evidence passages) is given a highest score. A synonym of movie, such as "motion picture" may be given a lower score but still higher than a synonym of the type "film" or "moving picture show." Instances of the exact matches and synonyms for each evidence passage may be compiled and used in a quantitative function to generate a score for the degree of matching of the evidence passage to the input question.

Thus, for example, a hypothesis or candidate answer to the input question of "What was the first movie?" is "The Horse in Motion." If the evidence passage contains the statements "The first motion picture ever made was 'The Horse in Motion' in 1878 by Eadweard Muybridge. It was a movie of a horse running," and the algorithm is looking for exact matches or synonyms to the focus of the input question, i.e. "movie," then an exact match of "movie" is found in the second sentence of the evidence passage and a highly scored synonym to "movie," i.e. "motion picture," is found in the first sentence of the evidence passage. This may be combined with further analysis of the evidence passage to identify that the text of the candidate answer is present in the evidence passage as well, i.e. "The Horse in Motion." These factors may be combined to give this evidence passage a relatively high score as supporting evidence for the candidate answer "The Horse in Motion" being a correct answer.

It should be appreciated that this is just one simple example of how scoring can be performed. Many other algorithms of various complexity may be used to generate scores for candidate answers and evidence without departing from the spirit and scope of the present invention.

In the synthesis stage 460, the large number of scores generated by the various reasoning algorithms are synthesized into confidence scores or confidence measures for the various hypotheses. This process involves applying weights to the various scores, where the weights have been determined through training of the statistical model employed by the QA pipeline 400 and/or dynamically updated. For example, the weights for scores generated by algorithms that identify exactly matching terms and synonym may be set relatively higher than other algorithms that are evaluating publication dates for evidence passages. The weights themselves may be specified by subject matter experts or learned through machine learning processes that evaluate the significance of characteristics evidence passages and their relative importance to overall candidate answer generation.

The weighted scores are processed in accordance with a statistical model generated through training of the QA pipeline 400 that identifies a manner by which these scores may be combined to generate a confidence score or measure for the individual hypotheses or candidate answers. This confidence score or measure summarizes the level of confidence that the QA pipeline 400 has about the evidence that the candidate answer is inferred by the input question, i.e. that the candidate answer is the correct answer for the input question.

The resulting confidence scores or measures are processed by a final confidence merging and ranking stage 470 which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/candidate answers (hereafter simply referred to as "candidate answers"). From the ranked listing of candidate answers, at stage 480, a final answer and confidence score, or final set of candidate answers and confidence scores, are generated and output to the submitter of the original input question via a graphical user interface or other mechanism for outputting information.

As shown in FIG. 4, in accordance with one illustrative embodiment, the QA pipeline 400 is augmented to work in conjunction with a MC base cartridge evaluation engine 490. The example shown in FIG. 4 assumes that the cognitive system in which the elements of FIG. 4 are provided has been trained using MC base cartridges in the manner described above.

In FIG. 4, the MC base cartridge evaluation engine 490 is shown as separate from the pipeline 400. However, rather than the MC base cartridge evaluation engine 490 being a separate entity as shown, elements of the MC base cartridge evaluation engine 490 may be integrated into the logic of one or more of the stages 410-480 of the QA pipeline 400. The QA pipeline 400 may provide patient attributes and optionally an indication of the medical condition (MC) class(es)/domain(s) with which the input question 410 is associated, such as may be identified from analysis of the input question 410 in stage 420.

The MC base cartridge evaluation engine 490, based on a MC class/domain identified for the input question 410 as communicated by stage 420 to the MC base cartridge evaluation engine 490, loads or ingests a medical condition base cartridge 498 in a pluggable manner such that the particular insight data structures for combinations of medical condition, treatment, clinical attributes, and the like, of the MC base cartridge 498 are plugged in and loaded by the MC base cartridge evaluation engine 490 via interface 492. More than one MC base cartridge 498 may be plugged in and loaded in this manner to configure the MC base cartridge evaluation engine 490 to evaluate patient information with regard to specific medical conditions and their corresponding potential treatments.

Patient attribute information received from the QA pipeline 400 as part of the input question, as well as the EMRs for the identified patient, may be input to the MC base cartridge evaluation engine 490 which then applies the specific values specified in the EMRs and patient attribute information to the particular logical combinations of features, weights, and the like, of the insight data structures of the plugged-in and loaded MC base cartridges 498. Based on the weighting values associated with the various features of the insight data structures, the correspondence of patient information to the features of the insight data structures, trained insight data structure based scoring logic 494, and the like, the MC base cartridge evaluation engine 490 generates a confidence score value for each treatment corresponding to a medical condition of the patient as indicated in the plugged-in and loaded MC base cartridges 498. For example, based on the medical condition cartridge 498, it may be determined that patients that are less than 60 years old can receive a corresponding treatment for the medical condition and thus, for an "inclusion feature score" if the patient is less than 60 years old, a value of "1" may be provided, while in the "exclusion feature score" this may result in a value of "0" indicating that the patient is not excluded from the treatment. Similarly, if the patient is 60 years old or older, the values would be reversed such that the inclusion feature score would be "0" and the exclusion feature score would be "1". Different weights may be assigned to different features as part of the information stored in the insight data structures of the plugged-in and loaded MC base cartridges 498. As noted above, these weights may be generated based on cross-correlation analysis, patient cohort analysis, positional statement grading values, and the like.

The insight data structure based scoring logic 494 applies the features of the insight data structures of the plugged-in and loaded MC base cartridges 498 to the patient attributes received from the question and topic analysis stage 420 logic, as well as patient information retrieved from patient EMRs for the patient from corpus or corpora 445, 447, and generates confidence scores for each of the treatments. These confidence scores are used by the treatment selection engine 496 to select a subset of the treatments as candidate treatment recommendations. For example, the treatment selection engine 496 may apply the confidence scores to one or more threshold values indicating which treatment recommendations have sufficient confidence to warrant further evaluation by the pipeline 400.

The resulting candidate treatment recommendations and their corresponding confidence scores are sent back to the QA pipeline 400, such as to the logic of the hypothesis generation stage 440. The logic of stage 440 may then perform evaluations of these candidate treatment recommendations based on the corpus or corpora 445, 447 in a manner such as previously described above to modify the confidence scores further for each candidate treatment recommendation, such as may be done using hypothesis and evidence scoring stage 450 logic. The results generated by logic 450 are then synthesized in stage 460 and final confidence merging and ranking 470 as well as final answer and confidence output generation 480 are performed in the manner previously described above. Thus, a treatment recommendation, or set of ranked treatment recommendations with corresponding confidence scores and possibly supporting evidence passages and the like, may be generated for an input question or request 410 using a pluggable framework and medical condition specific base cartridges.

Figure 5:
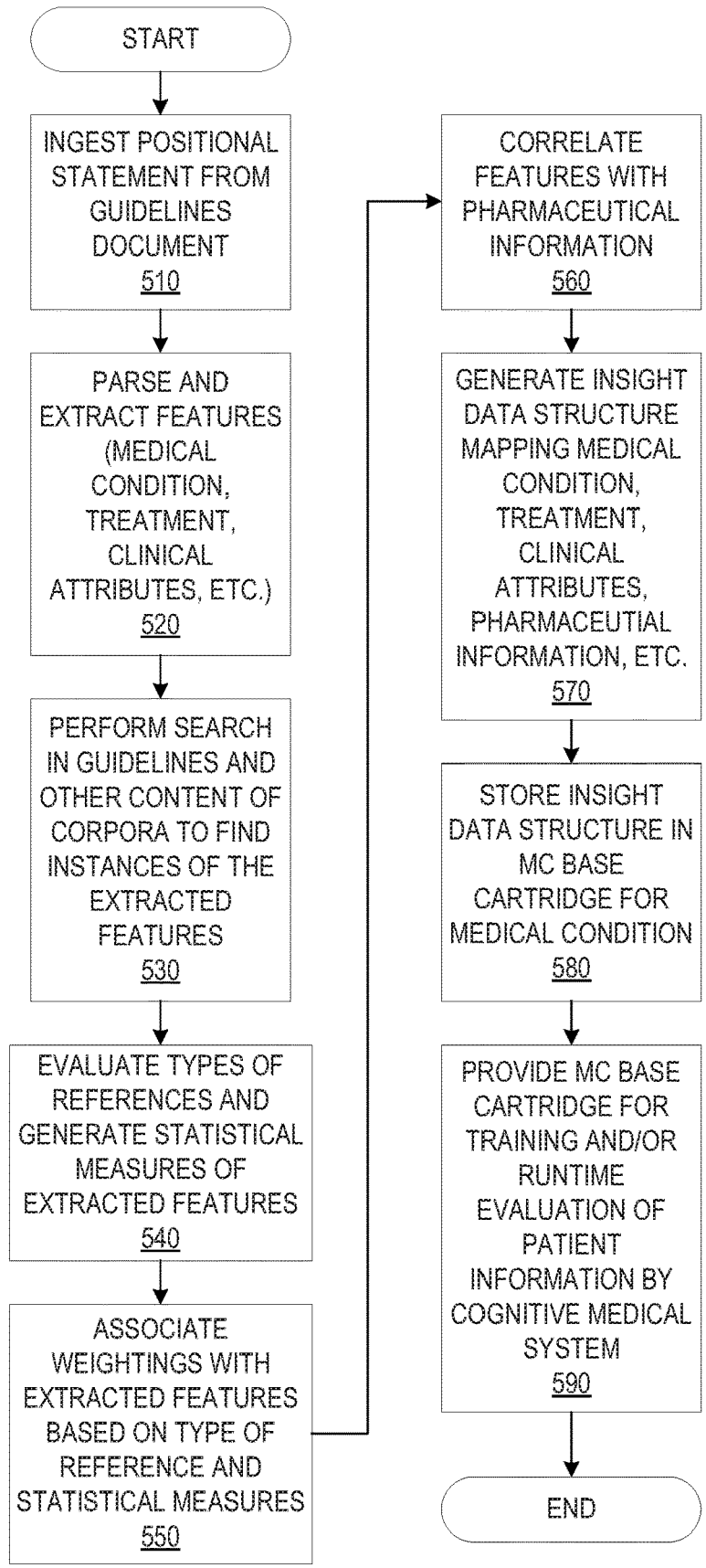
FIG. 5 is a flowchart outlining an example operation for cognitively building a medical condition base cartridge in accordance with one illustrative embodiment.

FIG. 5 is a flowchart outlining an example operation for cognitively building a medical condition base cartridge in accordance with one illustrative embodiment. As shown in FIG. 5, the operation starts with the ingestion of a positional statement from a medical treatment guidelines document (step 510). It should be noted that while the example assumes a positional statement of a guidelines document is being ingested, any portion of natural language content that is associated with a medical condition and treatment may be used without departing from the spirit and scope of the present invention. Moreover, it should be appreciated that this operation may be initiated in response to any triggering condition. For example, the operation may be performed as part of any ingestion operation initiated by an ingestion engine of a cognitive system. Such ingestion operations may be initiated as part of an initial configuration of the cognitive system, in response to changes made to documents of the corpus or corpora, in response to a user request to perform ingestion, in response to a timed or scheduled operation, or the like. In one illustrative embodiment, when a medical treatment guidelines document is modified or added to a corpus, the medical treatment guidelines document is ingested by the ingestion engine which includes initiating the operation outlined in FIG. 5 for each positional statement in the medical treatment guidelines document.

The ingestion of the positional statement includes the parsing and analyzing of the natural language content of the positional statement to extract the features of the positional statement, such as the medical condition referenced, the treatment(s) referenced, the clinical attributes referenced (e.g., medical condition, treatment, and patient attributes), and the like (step 520). These extracted features together constitute an initial insights data structure generated from the positional statement.

The extracted features are used as a basis for performing a search for similar instances of references to these features in the medical treatment guidelines document and other content of one or more corpora (step 530). For each instance, the type of reference to the feature is evaluated based on surrounding text analysis and statistical measures of the instances of the references to the extracted features are calculated (step 540). Weighting values are determined for the various extracted features based on the type of references to these extracted features found in the documents of the corpus or corpora and the statistical measures associated with the extracted features (step 550). As noted above, the weighting values may further be determined based on patient cohort analysis, positional statement grading values, and the like. Thus, each feature of an insight data structure may have one or more weighting values associated with it. In a case where a single weighting value is used with each feature, the weighting value may be determined based on a combination of one or more of the cross-correlation weighting value determination, patient cohort analysis based modification/adjustment of the weighting value, and positional statement grading value based modification/adjustment of the weighting value, for example. Alternatively, a separate type of weighting value may be provided as generated based on the separate types of analysis and associated with each feature.

In addition, the extracted features may be correlated with pharmaceutical information for any pharmaceuticals associated with the treatment referenced in the extracted features (step 560). A final insight data structure is generated that maps the medical condition, treatment, clinical attributes, pharmaceutical information, etc., and has the calculated weighting values associated with each of the extracted features (step 570). The insight data structure is stored in the medical condition base cartridge for the medical condition, which in turn is stored as part of the medical condition base cartridge repository (step 580). The stored medical condition base cartridge may then be provided to the cognitive system for training of the cognitive system and/or runtime evaluation of patient information by the cognitive system based on the knowledge represented in the insight data structures of the medical condition base cartridge (step 590). The operation then terminates. It should be appreciated that while FIG. 5 shows the operation terminating, the operation may be repeated for each ingested portion of natural language content, e.g., positional statement, such that multiple insight data structures for one or more medical condition base cartridges may be generated and stored in the medical condition base cartridge repository and provided to the cognitive system for training/runtime operation.

Figure 6:
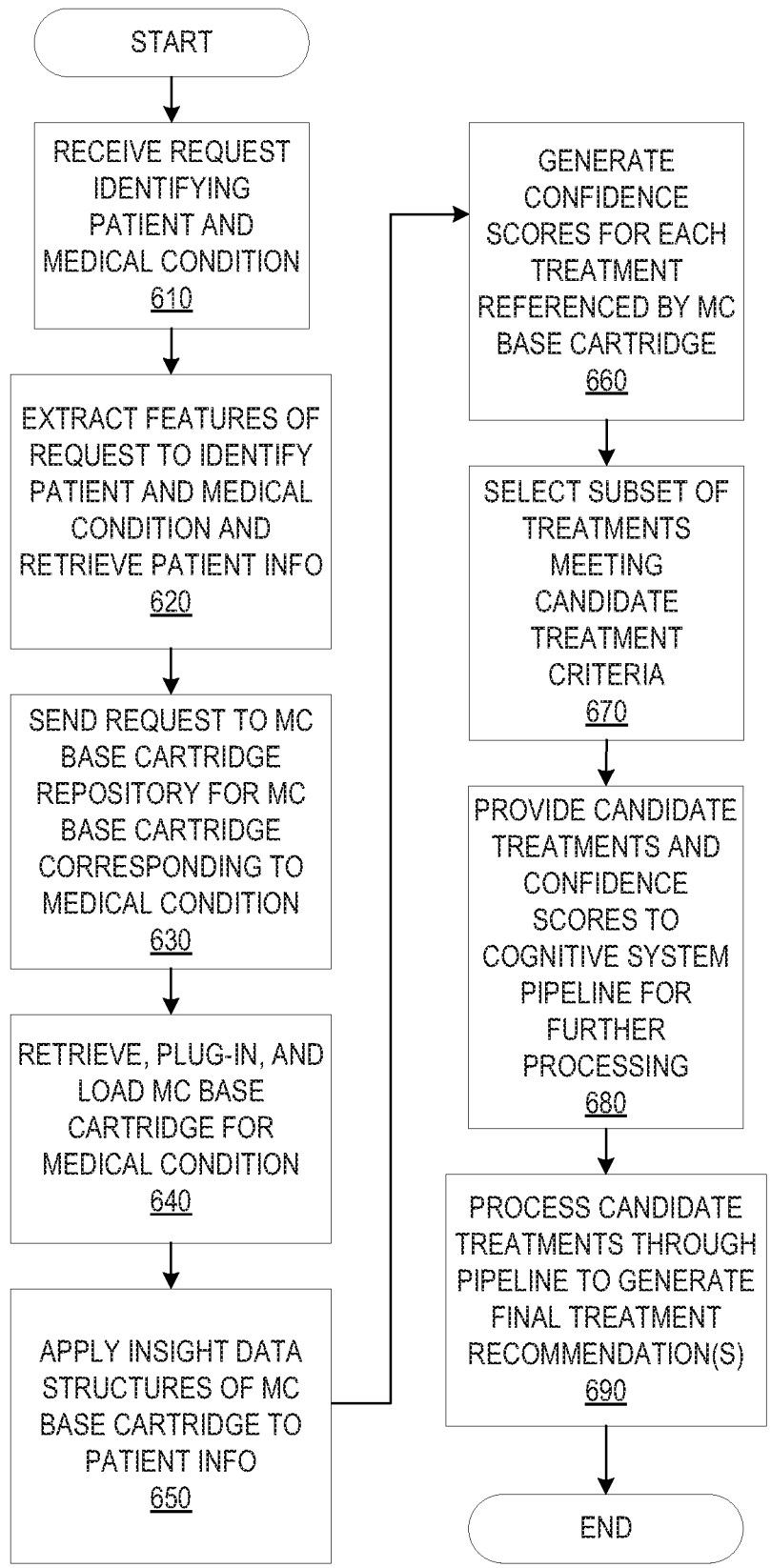
FIG. 6 is a flowchart outlining an example operation for implementing a medical condition base cartridge when performing runtime cognitive operations on patient information in accordance with one illustrative embodiment.

FIG. 6 is a flowchart outlining an example operation for implementing a medical condition base cartridge when performing runtime cognitive operations on patient information in accordance with one illustrative embodiment. As shown in FIG. 6, the operation starts by receiving a request, or input question, which identifies the patient for which the request/input question is being submitted and optionally a medical condition for which the patient is to be evaluated (step 610). It should be noted that in some cases, the medical condition need not be specified and instead the medical conditions may be obtained from patient EMR data or other input that indicates the medical condition(s) for which the patient is being evaluated.

Features are extracted from the request to identify the patient and, optionally, the medical condition (step 620). In addition, patient information for the identified patient may be retrieved, e.g., patient EMR data. A request is then sent to the MC base cartridge repository for the MC base cartridge corresponding to the identified medical condition for which the patient is being evaluated (step 630). The corresponding MC base cartridge is retrieved, plugged-into the pluggable framework of the cognitive system, and loaded by the cognitive system (step 640)

The insight data structures present in the MC base cartridge are then applied to the patient information retrieved for the patient (step 650). This may include patient attributes submitted along with the original request, such as may be entered by a user as part of a current evaluation of the patient, as well as stored patient information as may be present in one or more patient electronic medical records (EMRs) and the like. The patient information is compared to the various features associated with the insight data structures, used to determine matching between the features of the insight data structures and the attributes of the patient specified in the patient attributes and patient EMR data, and then score the treatments associated with the insight data structures based on this degree of matching with the various features of the insight data structures and the weighting values associated with the features. These scores are used to generate confidence scores for each of the treatments referenced by the MC base cartridge (step 660).

Based on the confidence scores associated with each of the treatments referenced by the MC base cartridge, a subset of treatments meeting candidate treatment criteria is selected (step 670). This candidate treatment criteria may comprise, for example, one or more threshold values indicating a required level of confidence for selection of the treatment as a candidate treatment for the particular patient. Thus, if a treatment referenced by the MC base cartridge has, for this patient, a confidence score equal to or greater than the threshold value representing the candidate treatment criterion, then the treatment may be selected as a candidate treatment for further processing.

The candidate treatments and their corresponding confidence scores are provided to the cognitive system pipeline for further processing (step 680). This further processing may comprise further hypothesis processing and supporting evidence evaluation to further refine the confidence scores associated with the candidate treatments. For example, further searching of one or more corpora may be performed to identify other supporting evidence passages that support or even refute the treatment as being applicable to the particular patient. This processing results in a final set of confidence scores associated with candidate treatments which may then be ranked relative to one another. The ranked candidate treatments may be categorized into different categories of treatments, such as those that are highly recommended, those that are worth consideration, and those that should not be considered for this patient. A final treatment recommendation, or a set of ranked treatment recommendations with corresponding categories may be generated and provided to the source of the original request (step 690). The operation then terminates.

Thus, in accordance with one aspect of the illustrative embodiments, mechanisms are provided for generating pluggable medical condition base cartridges that provide the basic knowledge for evaluating input factors to generate various decision support outputs regarding a medical condition, such as medical treatment recommendations or the like. These medical condition base cartridges provide mechanisms for implementing in logic the base knowledge for a medical condition, e.g., knowledge from standard documents, positional statements, treatment guidelines, and the like.

As noted above, in a further aspect of the illustrative embodiments, mechanisms are provided for extending the medical condition base cartridge based on subject matter expert (SME) knowledge extensions. The illustrative embodiments provide mechanisms through which a SME may extend the automatically generated logic for a medical condition evaluation by a cognitive medical system, via automatically generated foundational medical condition base cartridges, to implement their own personal expertise and knowledge regarding the medical aspect of the cognitive medical evaluation, without having to have technical knowledge of how to implement such in a cognitive computing system.

Figure 7:
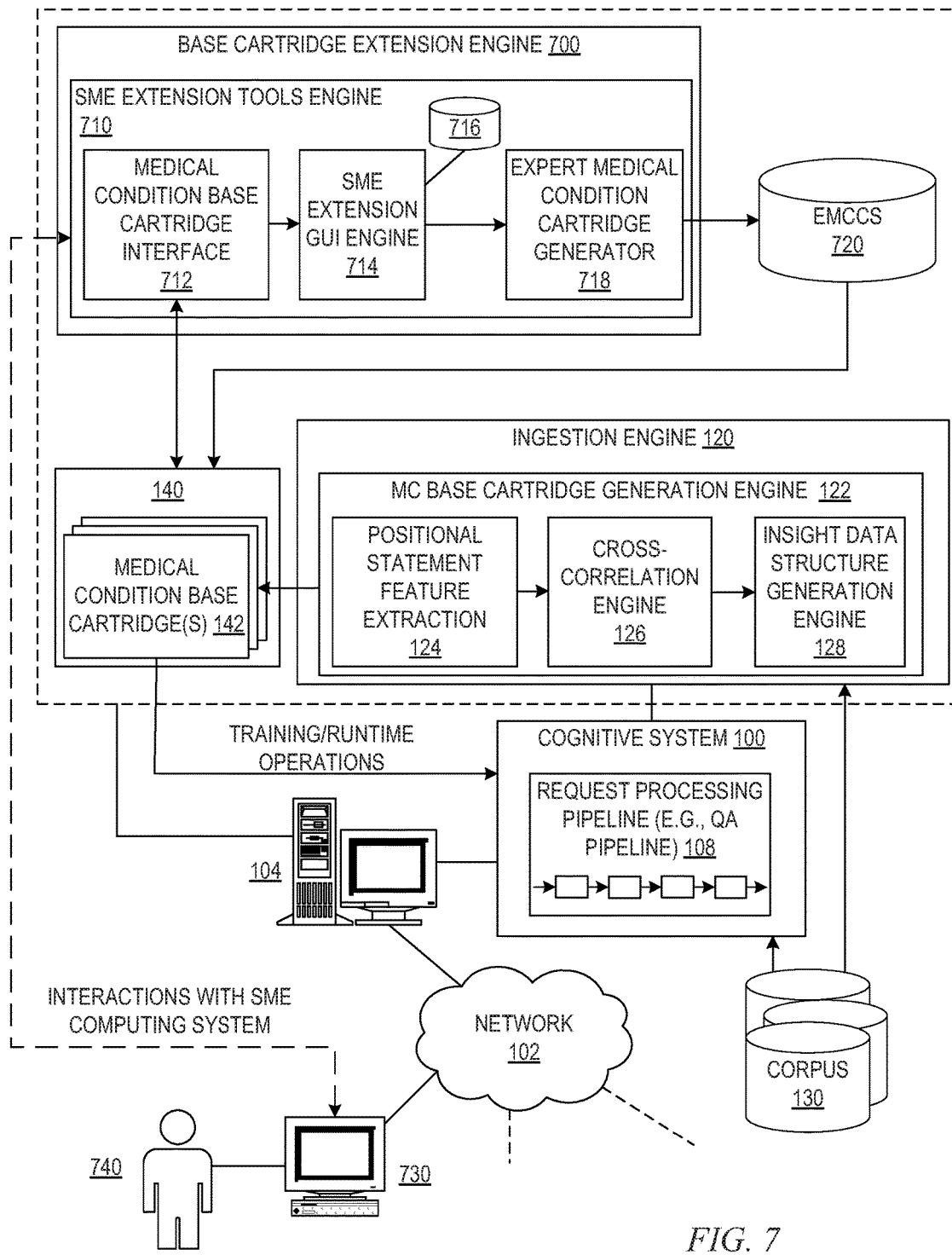
FIG. 7 is an example block diagram of a base cartridge extension engine in accordance with one illustrative embodiment.

FIG. 7 is an example block diagram of a base cartridge extension engine in accordance with one illustrative embodiment. Many of the elements shown in FIG. 7 are similar to those shown in FIG. 1 and described above, and thus, perform similar operations as previously described with regard to generating a medical condition base cartridge. Additional elements shown in FIG. 7 are directed to the mechanisms of some illustrative embodiments that support functionality for extending a medical condition base cartridge to include expert based extensions of the medical condition base cartridge that may be generated by one or more subject matter experts (SMEs).

As shown in FIG. 7, in addition to the elements of FIG. 1 previously described above, further illustrative embodiments provide a base cartridge extension engine 700 providing SME extension tools engine 710 for providing software based tools through which a SME may extend a medical condition base cartridge 142 in repository 140. The SME extension tools engine 710 comprises a medical condition base cartridge interface 712 through which medical condition base cartridges 142 may be retrieved from the repository 140 and presented via one or more Graphical User Interfaces (GUIs) to a user, which for purposes of this description will be assumed to be an SME. The SME extension tools engine 710 further includes an SME extension GUI engine 714 that comprises logic for generating GUIs to present medical condition base cartridge 142 details to the SME and further to provide GUI elements to permit the SME to extend the knowledge of the medical condition base cartridge 142 with the SME's own knowledge about the medical condition, treatments, patient attributes of importance to the evaluation and/or treatment of the medical condition, and the like.

The SME extension tools engine 710 further provides an expert medical condition cartridge (EMCC) generator 718 which provides logic for generating an EMCC based on the medical condition base cartridge and the extensions provided by the SME via the SME extension GUI engine 714. The EMCCs 720 generated by the EMCC generator 718 may be stored in the repository 140 either separately or in conjunction with the medical condition base cartridges 142. As with the medical condition base cartridges 142, the EMCCs 720 may be retrieved from the repository 140 and utilized by a cognitive system 100 when performing cognitive operations.

In accordance with one or more of the illustrative embodiments, a user, e.g., SME, may log onto or otherwise access the base cartridge extension engine 700 via the network 102 and a client computing device 730, referred to herein as a SME computing device 730. The base cartridge extension engine 700 may comprise logic for presenting to the SME computing device 730 graphical user interfaces (GUIs) for allowing the SME to access a medical condition base cartridge 142. For example, as noted above, a medical condition base cartridge may comprise various information and logic for implementing knowledge regarding a medical condition and potential treatments for the medical condition, as well as patient attributes of importance to the evaluation of the medical condition and the various treatments for the medical condition. This information may be present in the medical condition base cartridge 142 as insight data structures and/or trained models representing weighting values to be applied to various patient and medical condition attributes, e.g., the "clinical attributes" mentioned previously, with regard to potential treatments so as to be able to score the various treatments for a treating a patient with regard to the medical condition. Various other information may also be present in the medical condition base cartridge including, but not limited to, treatment characteristics, rules or criteria for evaluating clinical attributes for the various treatments, other medical logic, and the like, as previously described above. This information is made accessible via the base cartridge extension engine 700 and the GUIs the engine 700 provides to the SME computing device 730.

For example, in response to a request to access a particular medical condition base cartridge, group of medical condition base cartridges associated with a similar classification, medical condition, or group of medical conditions, or the like, the base cartridge extension engine 700 may provide SME extension tools engine 710 which includes a medical condition base cartridge interface 712 via which one or more medical condition base cartridges 142 may be retrieved from the repository 140 and the medical condition base cartridges 142 may be provided to the SME extension GUI engine 714 which may generate GUIs through which the information of the insight data structures of the medical condition base cartridge 142 may be output to the SME 740.

The SME extension GUI engine 714 provides GUIs through which the information present in a medical condition base cartridge 142 may be viewed and modified by an authorized individual, such as a SME 740. In so doing, the medical condition base cartridge 142 serves as a foundation of knowledge for a particular medical condition and to which the SME provides extensions using the SME extension tools engine 710. The tools may be various software logic elements that are implemented in connection with the SME extension GUI engine 714 to present to the SME various options, fields, and the like, via the GUIs by which the SME 740 may modify the information stored in the medical condition base cartridge 142, where such modifications may be additions to the information present in the medical condition base cartridge 142, modifications of information already present in the medical condition base cartridge 142, or deletions or removal of information items in the medical condition base cartridge 142. Depending on the desired implementation, any of the elements of the medical condition base cartridge 142 may be modifiable by an authorized SME 740 via the SME extension GUI engine 714.

For example, through the implementation of the SME extension GUI engine 714, GUIs are provided through which a SME 740 may view, for a medical condition base cartridge of a specific medical condition, the clinical attributes, treatments, various criteria for selecting treatments for the medical condition, medical logic, curated evidence for the various treatments, an established weighting model, and the like. Fields, GUI elements, and the like are provided through which the SME 740 may edit, add, and delete the medical condition base cartridge 142 information to provide additional knowledge of the SME 740 that may not be present in the medical condition base cartridge or otherwise reflects the SME's 740 own understanding of the medical condition, the associated clinical attributes, the treatments available for treating the medical condition, and the criteria by which to select a treatment for treating the medical condition based on a patient's attributes in patient information. Options presented to the SME 740 via the SME extension GUI engine 714 may further make use of resources 716 that provide information about clinical attributes, relationships between clinical attributes and corresponding values, and the like, that are generally known or specific to the particular medical condition associated with the MCBC 142. For example, the resources 716 may comprise data structures with patient attributes and their corresponding ranges of values, e.g., A1C ranges from 0 to 9 and is in units of percent such that a SME 740 may select A1C as an option from the GUI and select a corresponding value or range of values to associated with the A1C patient attribute when modifying or adding a patient attribute associated with a treatment evaluation for the medical condition. Using the foundational information from the MCBC 142, and the information available from resources 716, for example, the SME 740 may input expert-based treatment preferences, expert curated evidence, expert medical logic, more detailed clinical attribute information or alternative clinical attribute information, modifications to the weightings applied to clinical attributes by the weighting model in the medical condition base cartridge 142, and/or the like.

For example, assume that a medical condition base cartridge (MCBC) 142 is generated, using the mechanisms previously described, for a medical condition of "Type 2 Diabetes". In addition, assume that the MCBC 142 includes an insight data structure for a particular treatment option for the Type 2 Diabetes medical condition of the type {medical condition=Type 2 Diabetes, A1C>5.6 percent, gender=female, age>=50, treatment=drug Z, dosage=1 pill per day}. A SME 740 may view this information in a GUI generated by the SME extension GUI engine 714 and may modify the attributes of the insight data structure based on their own SME expert knowledge. For example, the SME 740 may determine that, based on their own experience, that the drug Z is a viable treatment option only for Type 2 Diabetes patients whose A1C is greater than 7 percent. Thus, the SME 740 may modify the attribute for A1C to be greater than 7 percent, e.g., A1C>7 percent. This modification may be stored as part of an extended medical condition cartridge (EMCC) 720 by the EMCC generator 718 based on the input received from the SME 740 via their SME computing device 730 and network 102.

In other examples, a SME 740 may augment the insight data structures present in the MCBC 142 by providing an additional SME 740 generated insight data structure, such as to provide an additional treatment option for the medical condition. For example, a SME 740 may know of a particular new treatment, e.g., a new medication, that the SME 740 may want reflected in the MCBC 142. Via the GUIs presented by the SME extension GUI engine 714, the SME 740 may enter information regarding a new treatment option and select from clinical attributes present in the MCBC 142 those that are important to the evaluation of whether the new treatment is appropriate for a particular patient. Moreover, the SME 740 may enter values or criteria by which to evaluate these particular clinical attributes with regard to the appropriateness of the treatment to particular patients for treating instances of the medical condition. Furthermore, the SME 740 may present medical logic, weighting values, and the like, to be applied to the various clinical attributes, such as part of a machine learning model or weighting model associated with the MCBC 142. These modifications again may be stored as part of an EMCC 720 by the EMCC generator 718.

In still other examples, the SME 740 may modify an insight data structure to remove criteria, clinical attributes, weighting values, or any other element that the SME 740 believes is not pertinent to the evaluation of a treatment option for the medical condition based on their own knowledge and experience. The removal may require that the SME 740 also make other modifications to the MCBC 142 insight data structures to accommodate the removal. Again, the resulting modified MCBC 142 may be stored as an EMCC 720 by the EMCC generator 718 based on the user input to the GUIs via the SME extension GUI engine 714.

In yet other examples, the SME 740 may designate some treatments to be more preferable than other treatments such that if both treatments are applicable to a particular patient, the one having preference from the SME 740 may be selected for providing a treatment recommendation to the medical practitioner requesting a treatment recommendation. For example, a designator, or field, may be provided in the GUIs through which the SME 740 may designate a preferred treatment, a weighting to be applied to one or more treatments so as to provide a relative preference of treatments, e.g., ranked 1 to 10 with 1 being the most preferred and 10 being the least preferred, or the like. Any mechanism by which an SME 740 may designate preferences of treatments may be used without departing from the spirit and scope of the present invention.

In addition, the SME 740 may identify portions of the corpus 130, other documentation from other sources accessible via the network 102, or upload or otherwise provide expert curated evidence to support the additions, modifications, or deletions that the SME 740 performs to the MCBC 142 to generate the EMCC 720. This expert curated evidence, or a link to such evidence, may be provided as part of the EMCC 720 and, in the case of electronic documentation that may not be part of the corpus 130, may be added to the corpus 130 automatically or after an evaluation process that may be initiated by the addition of the expert curated evidence to the EMCC 720.

Thus, the MCBC 142 retrieved from the repository 140 serves as a foundation of knowledge about the medical condition and its treatment options. The SME knowledge added to this foundation via the SME 740 input obtained from the SME computing system 730 via the SME extension GUI engine 714 supplements this foundational knowledge with knowledge that may not be able to be extracted from automated analysis of the corpus or corpora 130 by the MCBC generation engine 122, and which may be held by SMEs 740. As a result, the EMCC 720 represents expert knowledge expanding the foundational knowledge of the MCBC 142.

The generation of the MCBC 142 by the MCBC generation engine 122 may be performed without having to have specific institutional expertise, or SME expertise, in a particular medical condition since the knowledge represented by the medical condition base cartridge is obtained automatically from the corpus of corpora of electronic documentation 130, such as treatment guidelines, positional statements in trusted documentation, and the like. Given this foundation, a SME 740 needs to only make modifications to the foundation provided in the MCBC 142, to layer on top of the foundation their own personal expertise and knowledge regarding the particular medical condition and/or treatments for the medical condition.

For example, where a MCBC 142 may indicate that a particular patient attribute is more strongly indicative of a particular treatment being appropriate for the medical condition, the SME 740 may, based on their own particular knowledge, know that this patient attribute is not as significant as the documentation from the corpus 130 used to generate the medical condition base cartridge would seem to suggest, and may modify the weighting or strengths associated with that patient attribute and the corresponding treatment, delete the patient attribute, or add other patient attributes that are more indicative of the appropriateness of the treatment for particular patients. Moreover, a SME 740 may determine that some patient attributes were not included as factors when determining whether a particular treatment is appropriate or not, and may add those patient attributes along with a relative weighting or strength, contraindications, and the like. Still further, a SME 740 may know that certain medications that are part of a treatment for a particular medical condition may negatively interact with other medications and may add such information to the knowledge of the medical condition base cartridge, e.g., warnings, contraindications, etc. Many different tools may be provided by the SME extension tools engine 710 to the SME 740 to modify, remove, or add elements to the MCBC 142 via easily usable interfaces, e.g., GUIs generated by SME extension GUI engine 714, with the computing system logic of the SME extension tools engine 710 performing the work of translating the SME 740 input into new, modified, or removed elements of the medical condition cartridge. For example, the EMCC generator 718 may translate the SME 740 input into the new, modified, or removed elements of the medical condition cartridge and thereby generate an EMCC 720.

The EMCC 720 generated by the EMCC generator 718 may be stored in the medical condition cartridge repository 140. The EMCC may be stored as a separate and distinct structure from the MCBC 142 but including the MCBC 142 as a foundation, as a layered addition to the MCBC 142 that may be enabled/disabled based on a user request or configuration parameter, or as a separate EMCC 720 linked to the MCBC 142, such as via metadata or the like associated with the MCBC 142 and/or EMCC 720, such that the EMCC 720 may be retrievable when necessary and utilized in a cognitive system 100.

It should be appreciated that while FIG. 7 shows only a single SME 740 and corresponding SME computing device 730 being used to generate EMCCs 720 based on the foundational knowledge in the MCBCs 142, the illustrative embodiments are not limited to such. Rather, many different SMEs 740 may utilize their own associated SME computing devices 730 to generate their own sets of EMCCs 720 that encapsulate each SME's own personal knowledge and expertise. Thus, the repository 140 may store multiple different sets of EMCCs 720 generated by multiple different SMEs 740 using the mechanisms of the base cartridge extension engine 700 as discussed above. The sets of EMCCs 720 may be stored as groups or collections based on any common attribute. For example, the EMCCs 720 may be grouped by medical condition such that the same or similar medical condition, class of medical conditions, or the like, may represent one categorization or group of EMCCs 720 and/or MCBCs 142. In other embodiments, the EMCCs 720 may be grouped according to SME 740 that generated the EMCCs 720 such that separate groupings for each SME 740 are generated. Of course, multiple levels of nested groupings may also be utilized, such as an outer grouping based on medical condition and a nested grouping based on SME 740, for example. Such groupings or categorizations may be dynamically generated when necessary, e.g., when a user wishes to view of utilize only EMCCs 720 associated with a particular attribute that serves as a basis for generating the grouping.

As a result, when later being used by the cognitive system 100, such as to evaluate a patient's attributes to generate a treatment recommendation for example (such as described in connection with FIG. 3 above, for example), a user may choose to enable/disable the use of SME generated EMCCs 720. For example, in the request 308 sent by the user 306 in FIG. 3, the request may specify whether or not to enable EMCCs 720 or to rather operate only on MCBCs 142. In addition, the user 306 may select to enable/disable specific EMCCs 720 stored in the repository 140. For example, the user 30 may be presented with an interface via the medical cognitive system 300 through which the user may select which EMCCs 720 to utilize, which sets of EMCCs 720 to utilize based on a common attribute, e.g., same SME 740, same medical condition, same type or classification of medical condition, same or similar treatment, etc. In this way, a user may designate whether to use MCBCs 142, EMCCs 720, or a combination of the two, when performing evaluation of patient's information, e.g., patient attributes 318, to perform a cognitive operation on the patient's information, e.g., generating a treatment recommendation by the medical condition system 300. Based on the user's selections, corresponding MCBCs 142 and/or EMCCs 720 may be retrieved and loaded into the medical cognitive system 300 and used to evaluate the patient attributes 318 and provide a treatment recommendation 328.

Thus, as discussed previously, a large majority of the work required to generate logic for evaluating a medical condition is performed automatically by the mechanisms of the illustrative embodiment, e.g., by the MCBC generation engine 122, such that a knowledge structure for a medical condition providing a foundational knowledge from documentation may be generated, e.g., the MCBCs 142 in repository 140. Further mechanisms, e.g., the base cartridge extension engine 700 and SME extension tools engine 710, allow for a relatively smaller expenditure of effort on the part of a SME 740 to augment this foundational knowledge by providing the SME's own expert knowledge, such as via GUIs provided by the SME extension GUI engine 714 to the SME computing device 730, as an extension of this automatically generated foundational knowledge about the medical condition and its treatment options, which may then be stored as an EMCC 720 in the repository 140. Moreover, the foundational knowledge in the MCBCs 142 is reusable by various SMEs 740 such that each SME 740 may tailor the knowledge of a medical condition to their own experiences.

Figure 8:
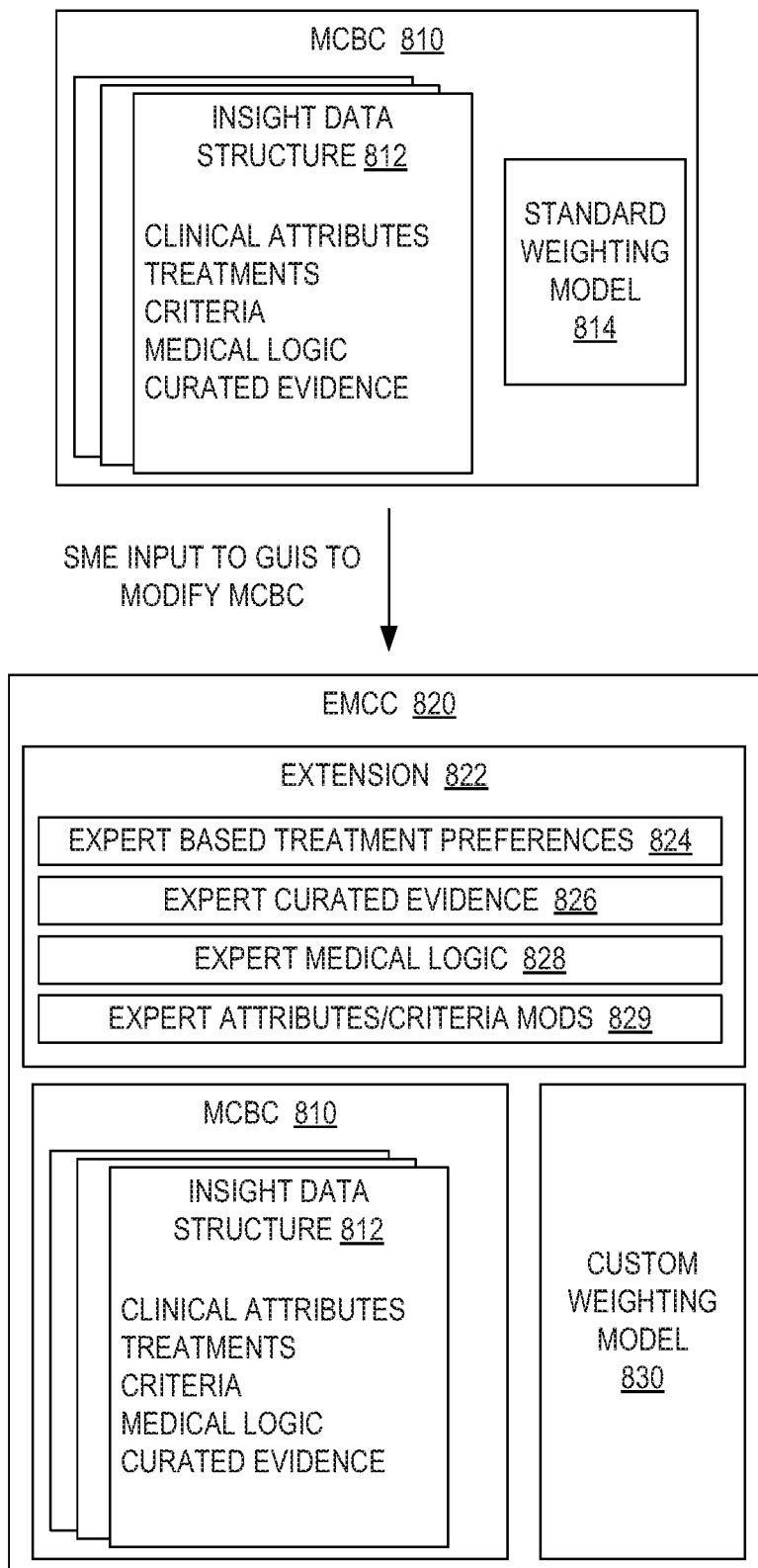
FIG. 8 is an example diagram illustrating a correlation between a medical condition base cartridge and an expert medical condition cartridge in accordance with one illustrative embodiment.

FIG. 8 is an example diagram illustrating a correlation between a medical condition base cartridge and an expert medical condition cartridge in accordance with one illustrative embodiment. As shown in FIG. 8, the medical condition base cartridge (MCBC) 810 comprises various automatically acquired information elements from the cognitive analysis of a corpus which results in one or more insight data structures 812. Each insight data structure 812 may be associated with a different treatment option for treating the medical condition associated with the MCBC 810 including various clinical attributes, treatment attributes, criteria for the treatment to be applicable to a particular patient, medical logic, curated evidence that supports the other elements of the insight data structure as identified from the corpus, and the like. A standard weighting model 814 may also be provided as part of the MCBC 810 that specifies the weighting values to be applied to different clinical attributes, to the various possible treatments, and the like, for evaluating which treatment to recommend for a patient. For example, as described in commonly assigned and co-pending U.S. patent application Ser. No. 15/262,311, the standard weighting algorithm may provide weights to be applied to aggregate clinical attributes into medical condition independent scoring values that may be used by a medical condition independent cognitive system to select a treatment recommendation or perform other cognitive operations.

The expert medical condition cartridge (EMCC) 820 provides an extension 822 to the MCBC 810 that includes knowledge provided by a SME and represented in a structured manner in association with the MCBC 810 as additional linked knowledge structures. In the depicted example, the extension 822 comprises expert based treatment preference information 824, expert curated evidence 826, expert medical logic 828, and expert supplied modifications to attributes/criteria 829 for evaluating one or more of the treatments associated with insight data structures 812 of the MCBC 810. In addition, the extension 822 may comprise a customized weighting model 830 where the SME has modified the weighting values associated with the various clinical attributes and/or treatments.

While the depiction in FIG. 8 shows the extension 822 enveloping the MCBC 810, this is only one example where the extension 822 and MCBC 810 together constitute the EMCC 820. In other illustrative embodiments, the extension 822 may be a separate knowledge structure from the MCBC 810 which may be stored separately and linked to the MCBC 810, such as by way of metadata in one or both of the MCBC 810 and EMCC 820.

Figure 9A:
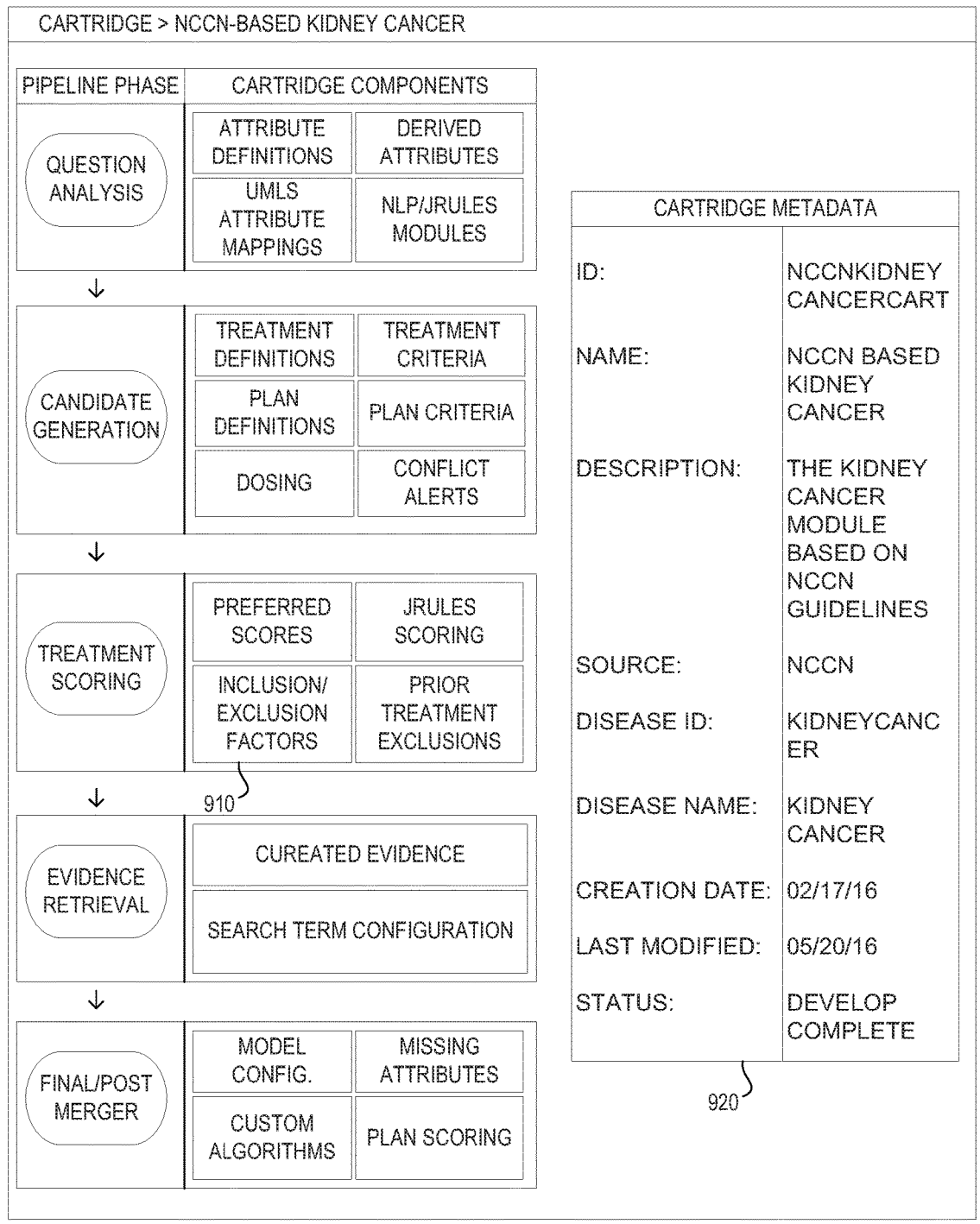

FIGS. 9A-9C are example diagrams of graphical user interfaces associated with SME extension tools in accordance with one illustrative embodiment. FIG. 9A is an example diagram illustrating a high level GUI comprising GUI elements for selecting components of a medical condition base cartridge that may be extended by input from a SME. For example, as shown in FIG. 9A, these components are categorized into different stages of the cognitive system's pipeline, e.g., question analysis, candidate treatment recommendation generation (candidate generation), candidate treatment recommendation scoring (treatment scoring), evidence retrieval, and final/post merger. In each category, there are one or more cartridge components that may be altered by the SME through this GUI by selecting the corresponding component that the SME wishes to modify. Thus, for example, a SME may choose to modify the inclusion/exclusion factors of a MCBC which are used for during treatment scoring and thus, the SME may select element 910 in FIG. 9A to thereby proceed to another GUI, such as that shown in FIG. 9B, where the SME may add, modify, or delete inclusion/exclusion factors so as to generate an extended medical condition cartridge (EMCC). Also shown in FIG. 9A is a portion 920 where metadata about the MCBC/EMCC is shown for reference and includes such information as the ID, name, description, source, medical condition (disease identifier), medical condition display name, the creation date of the MCBC, the last modified date, and the current status of the MCBC/EMCC.

FIG. 9B is an example diagram illustrating a GUI through which the SME may submit inclusion/exclusion factor additions, modifications, or deletions, such as in response to selecting element 910 in FIG. 9A, for example. For example, a SME may, via the GUI in FIG. 9B, enter an inclusion/exclusion factor for a treatment containing high-dose interleukin that the treatment should be almost completely excluded (0.9 exclusion factor where 1.0 represents full exclusion of the treatment) when the patient has a Cardio-Vascular Function risk (see element 930 in FIG. 9B). The example GUI in FIG. 9B further shows that lower levels of exclusion for other patient attributes may also be specified through interaction by a SME with the GUI. It should be appreciated that the SME may add to, or delete from, this listing of exclusion factors as desired. Moreover, the SME may specify inclusion factors as well as exclusion factors without departing from the spirit and scope of the present invention.

FIG. 9C is an example diagram illustrating a GUI through which a SME may specify or obtain information about how an attribute of a MCEE is derived from other combinations of attributes. For example, as shown in FIG. 9C, the entry 940 indicates that downstream logic can base criteria on the attribute "HadTKI." The depicted GUI shows that the attribute "HadTKI" is derived by checking whether the patient had any one of 10 prior treatments, i.e. PriorTargetedRegimen=[71200, 71201, 71202, . . . ] This allows for simplification of downstream logic by using an attribute that was derived from other more complex logic. Via the GUI mechanism shown here, a SME is presented with such information and can add, modify, or delete such derived attributes.

Figure 10:
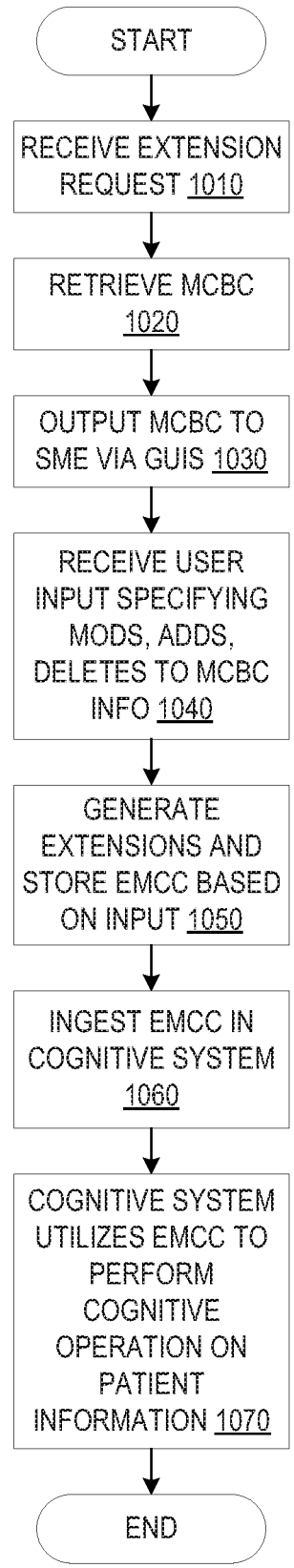
FIG. 10 is a flowchart outlining an example operation for extending a medical condition base cartridge in accordance with one illustrative embodiment.

FIG. 10 is a flowchart outlining an example operation for extending a medical condition base cartridge in accordance with one illustrative embodiment. The operation outlined in FIG. 10 may be implemented, for example, by the base cartridge extension engine 700 in FIG. 7, for example. It should be appreciated that while FIG. 10 depicts an operation be performed with regard to a single medical condition base cartridge and associated expert medical condition cartridge, the illustrative embodiments are not limited to such and the operation shown in FIG. 10 may be performed sequentially or in parallel with a plurality of medical condition base cartridges and/or expert medical condition cartridges without departing from the spirit and scope of the present invention.

As shown in FIG. 10, the operation starts with receiving a request, such as from a SME or other authorized user, to extend a medical condition base cartridge (MCBC) (step 1010). The request may specify the MCBC specifically, a class or type of medical condition with which the MCBC is associated, a treatment with which the MCBC is associated, or any other attribute of a MCBC that may be used to identify the MCBC. The corresponding MCBC is retrieved from the medical cartridge repository (step 1020) and the detailed information about the MCBC is output via one or more GUIs to the SME or authorized user via an associated computing device (step 1030).

User input is received via the output GUIs providing the detailed information about the MCBC that specifies modifications, additions, and/or deletions to the MCBC insight data structures (step 1040). The modifications, additions, and/or deletions represent SME knowledge that augments and extends the knowledge represented in the MCBC. The modifications, additions, and/or deletions are used to generate extensions to the insight data structures of the MCBC which are then stored as an extended medical condition cartridge (EMCC) associated with the MCBC (step 1050). As previously noted above, the EMCC may encapsulate the MCBC, be stored as an extension to the MCBC stored in association with the MCBC, or otherwise stored as a separate knowledge structure that is linked to the MCBC, such as via metadata or any other linkage between data structures.

The stored EMCC may then be ingested by a cognitive system (step 1060) and utilized by the cognitive system to perform a cognitive medical operation, such as a diagnostic operation, treatment recommendation operation, or the like (step 1070). It should be appreciated that the ingestion and utilization of the EMCC by the cognitive system may be specifically enabled/disabled by user selections as noted previously. The operation then terminates.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement the method, comprising:

generating, by the data processing system, a medical condition base cartridge (MCBC) comprising basic insight data structures for a medical condition at least by performing cognitive processing of natural language content in a corpus by a cognitive computing device implementing natural language processing computer logic to extract patient attributes and treatment information associated with the medical condition from the natural language content in the corpus;

presenting, by the data processing system, to a user, information stored in the basic insight data structures of the MCBC, via at least one interface;

receiving, by the data processing system, user input to the at least one interface, the user input indicating at least one of a modification of, addition to, or deletion of, a portion of the information presented to generate an extension to the MCBC;

storing, by the data processing system, the extension to the MCBC as an expert medical condition cartridge (EMCC) in association with the MCBC in a repository; and inputting, by the data processing system, the EMCC to a medical cognitive system to perform a medical cognitive operation on patient information based on the EMCC, wherein the medical cognitive operation comprises training the medical cognitive system, to generate a trained medical cognitive system, by executing a machine learning operation in which the EMCC is a ground truth data structure, during execution of the machine learning operation, and specifies a correct treatment recommendation for patients having the patient attributes and the medical condition.

2. The method of claim 1, wherein the MCBC is associated with a plurality of different EMCCs in the repository such that the MCBC is a basis for each EMCC in the plurality of different EMCCs.

3. The method of claim 1, wherein the EMCC is stored in association with the MCBC in the repository as one of a separate data structure with a link to the MCBC, a separate data structure that encompasses content of the MCBC, or a layer addition to the MCBC that is enabled/disabled according to a configuration parameter or user request.

4. The method of 1, wherein presenting information stored in the basic insight data structures of the MCBC via at least one interface to the user comprises:
retrieving resource information indicating standardized associations of clinical attributes with one of the medical condition or a treatment of the medical condition; and
presenting the resource information in association with interface elements for selecting or modifying the resource information.

5. The method of claim 1, wherein the user input to the at least one interface adds or modifies medical logic or weighting values to be applied by a cognitive system when evaluating clinical attributes of a patient electronic medical record.

6. The method of claim 1, wherein the user input to the at least one interface specifies a preference of the user for a specific treatment over other potential treatments for the medical condition.

7. The method of claim 1, wherein the user input to the at least one interface specifies user curated evidence documents from a corpus of documentation that supports a preference of a specific treatment over other potential treatments for the medical condition.

8. The method of claim 1, further comprising receiving, by the data processing system, a request from a user to access a medical condition cartridge associated with the medical condition, wherein the request specifies the medical condition, and wherein the presenting, receiving, and storing operations are performed responsive to receiving the request.

9. The method of claim 1, further comprising:
receiving, by the data processing system, a user request that requests a treatment recommendation for a specified patient and a specified medical condition associated with the specified patient, wherein the user request includes an indicator of whether or not to enable use of EMCCs by the medical cognitive system; and
processing, by the medical cognitive system, patient information associated with the specified patient based on the EMCC in response to the user request enabling the use of EMCCs by the medical cognitive system, to thereby generate a treatment recommendation for the specified patient and the specified medical condition.

10. The method of claim 1, further comprising:
automatically generating, by the trained medical cognitive system, a treatment recommendation for a patient by processing patient medical information for the patient at least by performing a cognitive computing evaluation of the patient medical information, thereby generating the treatment recommendation for the patient.

11. A computer program product comprising a non-transitory computer readable medium having a computer readable program stored therein, wherein the computer readable program, when executed on a computing device, causes the computing device to:
generate a medical condition base cartridge (MCBC) comprising basic insight data structures for a medical condition at least by performing cognitive processing of natural language content in a corpus by a cognitive computing device implementing natural language processing computer logic to extract patient attributes and treatment information associated with the medical condition from the natural language content in the corpus;
present, to a user, information stored in the basic insight data structures of the MCBC, via at least one interface;
receive user input to the at least one interface, the user input indicating at least one of a modification of, addition to, or deletion of, a portion of the information presented to generate an extension to the MCBC;
store the extension to the MCBC as an expert medical condition cartridge (EMCC) in association with the MCBC in a repository; and
input the EMCC to a medical cognitive system to perform a medical cognitive operation on patient information based on the EMCC, wherein the medical cognitive operation comprises training the medical cognitive system, to generate a trained medical cognitive system, by executing a machine learning operation in which the EMCC is a around truth data structure, during execution of the machine learning operation, and specifies a correct treatment recommendation for patients having the patient attributes and the medical condition.

12. The computer program product of claim 11, wherein the MCBC is associated with a plurality of different EMCCs in the repository such that the MCBC is a basis for each EMCC in the plurality of different EMCCs.

13. The computer program product of claim 11, wherein the EMCC is stored in association with the MCBC in the repository as one of a separate data structure with a link to the MCBC, a separate data structure that encompasses content of the MCBC, or a layer addition to the MCBC that is enabled/disabled according to a configuration parameter or user request.

14. The computer program product of 11, wherein the computer readable program further causes the computing device to present information stored in the basic insight data structures of the MCBC via at least one interface to the user at least by:
retrieving resource information indicating standardized associations of clinical attributes with one of the medical condition or a treatment of the medical condition; and
presenting the resource information in association with interface elements for selecting or modifying the resource information.

15. The computer program product of claim 1, wherein the user input to the at least one interface adds or modifies medical logic or weighting values to be applied by a cognitive system when evaluating clinical attributes of a patient electronic medical record.

16. The computer program product of claim 11, wherein the user input to the at least one interface specifies a preference of the user for a specific treatment over other potential treatments for the medical condition.

17. The computer program product of claim 11, wherein the user input to the at least one interface specifies user curated evidence documents from a corpus of documentation that supports a preference of a specific treatment over other potential treatments for the medical condition.

18. The computer program product of claim 11 wherein the computer readable program further causes the computing device to receive a request from a user to access a medical condition cartridge associated with the medical condition, wherein the request specifies the medical condition, and wherein the presenting, receiving, and storing operations are performed responsive to receiving the request.

19. The computer program product of claim 11, wherein the computer readable program further causes the computing device to:

automatically generate, by the trained medical cognitive system, a treatment recommendation for a patient by processing patient medical information for the patient at least by performing a cognitive computing evaluation of the patient medical information, thereby generating the treatment recommendation for the patient.

20. An apparatus comprising:

a processor; and a memory coupled to the processor, wherein the memory comprises instructions which, when executed by the processor, cause the processor to:

generate a medical condition base cartridge (MCBC) comprising basic insight data structures for a medical condition at least by performing cognitive processing of natural language content in a corpus by a cognitive computing device implementing natural language processing computer logic to extract patient attributes and treatment information associated with the medical condition from the natural language content in the corpus;

present, to a user, information stored in the basic insight data structures of the MCBC, via at least one interface;

receive user input to the at least one interface, the user input indicating at least one of a modification of addition to, or deletion of, a portion of the information presented to generate an extension to the MCBC;

store the extension to the MCBC as an expert medical condition cartridge (EMCC) in association with the MCBC in a repository; and input the EMCC to a medical cognitive system to perform a medical cognitive operation on patient information based on the EMCC, wherein the medical cognitive operation comprises training the medical cognitive system, to generate a trained medical cognitive system, by executing a machine learning operation in which the EMCC is a ground truth data structure, during execution of the machine learning operation, and specifies a correct treatment recommendation for patients having the patient attributes and the medical condition.

\* \* \* \* \*